(12) United States Patent
Alexander et al.

(10) Patent No.: US 11,516,443 B2
(45) Date of Patent: *Nov. 29, 2022

(54) SYSTEM AND METHOD FOR ACQUIRING IMAGES OF MEDICATION PREPARATIONS

(71) Applicant: Becton, Dickinson and Company, Franklin Lakes, NJ (US)

(72) Inventors: Emily H. Alexander, Alpine, TX (US); Jerimiah G. Welch, Bellingham, WA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/345,285

(22) Filed: Jun. 11, 2021

(65) Prior Publication Data

US 2021/0306600 A1  Sep. 30, 2021

Related U.S. Application Data

(63) Continuation of application No. 16/725,084, filed on Dec. 23, 2019, now Pat. No. 11,064,164, which is a continuation of application No. 15/895,377, filed on Feb. 13, 2018, now Pat. No. 10,554,937, which is a
(Continued)

(51) Int. Cl.
*H04N 7/18* (2006.01)
*A61B 90/96* (2016.01)
*A61B 17/00* (2006.01)
*A61B 90/00* (2016.01)

(52) U.S. Cl.
CPC .............. *H04N 7/185* (2013.01); *A61B 90/96* (2016.02); *A61B 90/361* (2016.02); *A61B 2017/00973* (2013.01)

(58) Field of Classification Search
USPC ........................................................ 348/143
See application file for complete search history.

(56) References Cited

U.S. PATENT DOCUMENTS

| 3,587,856 A | 6/1971 | Lemelson |
| 3,627,423 A | 12/1971 | Knapp et al. |
| 3,734,286 A | 5/1973 | Simjian |

(Continued)

FOREIGN PATENT DOCUMENTS

| CA | 2477259 A1 | 9/2003 |
| EP | 1763810 A2 | 3/2007 |

(Continued)

OTHER PUBLICATIONS

Anderson, "A Narrative on the History of the Development of Telepharmacy in North Dakota from the Board of Pharmacy's Perspective Recorded by Excerpts from Board Minutes," Feb. 2006, pp. 1-5.

(Continued)

*Primary Examiner* — Behrooz M Senfi
(74) *Attorney, Agent, or Firm* — The Webb Law Firm

(57) ABSTRACT

A system for holding a camera for acquiring images of preparations includes a rail that can be mounted above a preparation surface. A camera carrier couples a camera with the rail such that the camera is movable relative to the rail and such that the camera can acquire images of preparations on the preparation surface.

15 Claims, 17 Drawing Sheets

Related U.S. Application Data continuation of application No. 13/097,575, filed on Apr. 29, 2011, now Pat. No. 9,930,297.

(60) Provisional application No. 61/330,146, filed on Apr. 30, 2010.

(56) References Cited

U.S. PATENT DOCUMENTS

| | | |
|---|---|---|
| 3,914,058 A | 10/1975 | Knapp et al. |
| 3,965,340 A | 6/1976 | Renner et al. |
| 3,966,332 A | 6/1976 | Knapp et al. |
| 3,970,643 A | 7/1976 | Kee Woo et al. |
| 4,017,157 A | 4/1977 | van Riet |
| 4,063,823 A | 12/1977 | Grat |
| 4,087,184 A | 5/1978 | Knapp et al. |
| 4,165,633 A | 8/1979 | Raisanen |
| 4,277,089 A | 7/1981 | Lockhart |
| 4,469,146 A | 9/1984 | Campbell et al. |
| 4,476,381 A | 10/1984 | Rubin |
| 4,549,205 A | 10/1985 | Misaki et al. |
| 4,628,193 A | 12/1986 | Blum |
| 4,653,010 A | 3/1987 | Figler et al. |
| 4,655,026 A | 4/1987 | Wigoda |
| 4,676,650 A | 6/1987 | Bjorndal et al. |
| 4,676,776 A | 6/1987 | Howson |
| 4,695,954 A | 9/1987 | Rose et al. |
| 4,790,118 A | 12/1988 | Chilcoate |
| 4,803,625 A | 2/1989 | Fu et al. |
| 4,804,273 A | 2/1989 | Tondello et al. |
| 4,810,243 A | 3/1989 | Howson |
| 4,823,982 A | 4/1989 | Aten et al. |
| 4,835,372 A | 5/1989 | Gombrich et al. |
| 4,839,675 A | 6/1989 | Owen |
| 4,847,764 A | 7/1989 | Halvorson |
| 4,850,009 A | 7/1989 | Zook et al. |
| 4,853,521 A | 8/1989 | Claeys et al. |
| 4,857,716 A | 8/1989 | Gombrich et al. |
| 4,860,899 A | 8/1989 | McKee |
| 4,879,650 A | 11/1989 | Kurimoto et al. |
| 4,918,604 A | 4/1990 | Baum |
| 4,972,657 A | 11/1990 | McKee |
| 5,014,875 A | 5/1991 | McLaughlin et al. |
| 5,031,642 A | 7/1991 | Nosek |
| 5,088,981 A | 2/1992 | Howson et al. |
| 5,094,786 A | 3/1992 | Nagashima et al. |
| 5,111,408 A | 5/1992 | Amjadi |
| 5,153,827 A | 10/1992 | Coutré et al. |
| 5,182,707 A | 1/1993 | Cooper et al. |
| 5,184,753 A | 2/1993 | Horak |
| 5,196,001 A | 3/1993 | Kao |
| 5,260,880 A | 11/1993 | Tump |
| 5,261,546 A | 11/1993 | Van Der Grift |
| 5,272,318 A | 12/1993 | Gorman |
| 5,308,930 A | 5/1994 | Tokutu et al. |
| 5,317,506 A | 5/1994 | Coutré et al. |
| 5,328,208 A | 7/1994 | Garrison |
| 5,337,919 A | 8/1994 | Spaulding et al. |
| 5,341,077 A | 8/1994 | Chen et al. |
| 5,341,854 A | 8/1994 | Zezulka et al. |
| 5,344,043 A | 9/1994 | Moulding et al. |
| 5,348,061 A | 9/1994 | Riley et al. |
| 5,365,343 A | 11/1994 | Knapp |
| 5,390,796 A | 2/1995 | Kerfoot, Jr. |
| 5,395,174 A | 3/1995 | Koch et al. |
| 5,401,059 A | 3/1995 | Ferrario |
| 5,404,227 A | 4/1995 | Sumita et al. |
| 5,405,048 A | 4/1995 | Rogers et al. |
| 5,416,695 A | 5/1995 | Stutman et al. |
| 5,416,706 A | 5/1995 | Hagenbuch |
| 5,442,146 A | 8/1995 | Bell et al. |
| 5,444,480 A | 8/1995 | Sumita |
| 5,444,539 A | 8/1995 | van der Grift |
| 5,468,110 A | 11/1995 | McDonald et al. |
| 5,480,062 A | 1/1996 | Rogers et al. |
| 5,502,944 A | 4/1996 | Kraft et al. |
| 5,508,499 A | 4/1996 | Ferrario |
| 5,511,594 A | 4/1996 | Brennan et al. |
| 5,516,475 A | 5/1996 | Wilson |
| 5,523,560 A | 6/1996 | Manique et al. |
| 5,568,262 A | 10/1996 | LaChapelle et al. |
| 5,583,948 A | 12/1996 | Shibayama |
| 5,593,267 A | 1/1997 | McDonald et al. |
| 5,597,995 A | 1/1997 | Williams et al. |
| 5,601,314 A | 2/1997 | Burns et al. |
| 5,643,212 A | 7/1997 | Coutré et al. |
| 5,646,912 A | 7/1997 | Cousin |
| 5,651,775 A | 7/1997 | Walker et al. |
| 5,713,485 A | 2/1998 | Liff et al. |
| 5,719,679 A | 2/1998 | Shimizu et al. |
| 5,720,154 A | 2/1998 | Lasher et al. |
| 5,721,433 A | 2/1998 | Kosaka |
| 5,747,744 A | 5/1998 | Kraft et al. |
| 5,753,868 A | 5/1998 | Diem |
| 5,758,095 A | 5/1998 | Albaum et al. |
| 5,771,657 A | 6/1998 | Lasher et al. |
| 5,780,778 A | 7/1998 | Schwartz et al. |
| 5,781,442 A | 7/1998 | Engleson et al. |
| 5,797,515 A | 8/1998 | Liff et al. |
| 5,833,866 A | 11/1998 | Brown |
| 5,836,867 A | 11/1998 | Speier et al. |
| 5,841,077 A | 11/1998 | Kolaci |
| 5,841,541 A | 11/1998 | Dlugos |
| 5,907,493 A | 5/1999 | Boyer et al. |
| 5,940,176 A | 8/1999 | Knapp |
| 5,941,867 A | 8/1999 | Kao |
| 5,963,136 A | 10/1999 | O'Brien |
| 5,966,457 A | 10/1999 | Lemelson |
| 5,969,317 A | 10/1999 | Espy et al. |
| 5,979,512 A | 11/1999 | McGregor et al. |
| 5,990,422 A | 11/1999 | Komori et al. |
| 6,000,828 A | 12/1999 | Leet |
| 6,005,959 A | 12/1999 | Mohan et al. |
| 6,006,828 A | 12/1999 | Kluth et al. |
| 6,021,380 A | 2/2000 | Fredriksen et al. |
| 6,068,156 A | 5/2000 | Liff et al. |
| 6,088,527 A | 7/2000 | Rybczynski |
| 6,113,578 A | 9/2000 | Brown |
| 6,181,982 B1 | 1/2001 | Yuyama et al. |
| 6,202,923 B1 | 3/2001 | Boyer et al. |
| 6,234,964 B1 | 5/2001 | Iliff |
| 6,260,023 B1 | 7/2001 | Seevers et al. |
| 6,330,491 B1 | 12/2001 | Lion |
| 6,345,207 B1 | 2/2002 | Nitta et al. |
| 6,347,486 B1 | 2/2002 | Badillet |
| 6,364,517 B1 | 4/2002 | Yuyama et al. |
| 6,384,348 B1 | 5/2002 | Haga et al. |
| 6,438,451 B1 | 8/2002 | Lion |
| 6,466,879 B1 | 10/2002 | Cantu et al. |
| 6,473,169 B1 | 10/2002 | Dawley et al. |
| 6,518,996 B1 | 2/2003 | Polidor et al. |
| 6,529,801 B1 | 3/2003 | Rosenblum |
| 6,535,637 B1 | 3/2003 | Wootton et al. |
| 6,542,902 B2 | 4/2003 | Dulong et al. |
| 6,551,391 B1 | 4/2003 | Gerhardt et al. |
| 6,564,121 B1 | 5/2003 | Wallace et al. |
| 6,574,580 B2 | 6/2003 | Hamilton |
| 6,581,798 B2 | 6/2003 | Liff et al. |
| 6,605,784 B2 | 8/2003 | Eigenmann et al. |
| 6,694,334 B2 | 2/2004 | DuLong et al. |
| 6,711,460 B1 | 3/2004 | Reese |
| 6,731,324 B2 | 5/2004 | Levy |
| 6,738,723 B2 | 5/2004 | Hamilton |
| 6,771,369 B2 | 8/2004 | Rzasa et al. |
| 6,775,602 B2 | 8/2004 | Gordon, Jr. et al. |
| 6,781,689 B2 | 8/2004 | Chiba |
| 6,810,355 B1 | 10/2004 | Kreidler et al. |
| 6,813,473 B1 | 11/2004 | Bruker |
| 6,814,255 B2 | 11/2004 | Liff et al. |
| 6,816,625 B2 | 11/2004 | Lewis, Jr. et al. |
| 6,873,725 B2 | 3/2005 | Xu |
| 6,877,530 B2 | 4/2005 | Osborne et al. |
| 6,915,823 B2 | 7/2005 | Osborne et al. |
| 6,920,094 B2 | 7/2005 | Komaki |
| 6,922,652 B2 | 7/2005 | Edwards et al. |

(56) References Cited

U.S. PATENT DOCUMENTS

| | | |
|---|---|---|
| 6,937,339 B2 | 8/2005 | Yamazaki et al. |
| 6,970,094 B2 | 11/2005 | Yamashita et al. |
| 6,975,924 B2 | 12/2005 | Kircher et al. |
| 6,990,463 B2 | 1/2006 | Walter et al. |
| 6,995,664 B1 | 2/2006 | Darling |
| 6,998,542 B2 | 2/2006 | Wallisch |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,070,097 B2 | 7/2006 | Blanford et al. |
| 7,096,212 B2 | 8/2006 | Tribble et al. |
| 7,107,106 B2 | 9/2006 | Engleson et al. |
| 7,117,902 B2 | 10/2006 | Osborne |
| 7,128,105 B2 | 10/2006 | Tribble et al. |
| 7,139,639 B2 | 11/2006 | Broussard et al. |
| 7,155,396 B2 | 12/2006 | Yuyama et al. |
| 7,163,035 B2 | 1/2007 | Khan et al. |
| 7,173,197 B1 | 2/2007 | Kasperek |
| 7,180,014 B2 | 2/2007 | Farber et al. |
| 7,194,336 B2 | 3/2007 | DiGianfilippo et al. |
| 7,209,891 B1 | 4/2007 | Addy et al. |
| 7,218,395 B2 | 5/2007 | Kaye et al. |
| 7,230,529 B2 | 6/2007 | Ketcherside, Jr. et al. |
| 7,240,699 B2 | 7/2007 | Osborne et al. |
| 7,247,002 B2 | 7/2007 | Albrecht et al. |
| 7,262,847 B2 | 8/2007 | Goodall et al. |
| 7,286,997 B2 | 10/2007 | Spector et al. |
| 7,297,108 B2 | 11/2007 | Iliff |
| 7,310,143 B2 | 12/2007 | Budd |
| 7,317,967 B2 | 1/2008 | DiGianfilippo et al. |
| 7,343,224 B2 | 3/2008 | DiGianfilippo et al. |
| 7,343,943 B2 | 3/2008 | Khan et al. |
| 7,357,045 B2 | 4/2008 | Rasmussen et al. |
| 7,363,115 B2 | 4/2008 | Anderson et al. |
| 7,375,294 B2 | 5/2008 | Kraft |
| 7,376,934 B2 | 5/2008 | Steinrisser et al. |
| 7,391,515 B2 | 6/2008 | Budd et al. |
| 7,457,685 B2 | 11/2008 | D'Silva |
| 7,478,513 B2 | 1/2009 | Baldwin |
| 7,493,263 B2 | 2/2009 | Helmus et al. |
| 7,499,581 B2 | 3/2009 | Tribble et al. |
| 7,530,497 B2 | 5/2009 | Knowles et al. |
| 7,536,843 B2 | 5/2009 | Djurle et al. |
| 7,554,042 B2 | 6/2009 | Gregerson et al. |
| 7,555,557 B2 | 6/2009 | Bradley et al. |
| 7,560,720 B2 | 7/2009 | Voigt et al. |
| 7,578,802 B2 | 8/2009 | Hickle |
| 7,581,953 B2 | 9/2009 | Lehmann et al. |
| 7,592,553 B2 | 9/2009 | Yuyama et al. |
| 7,597,247 B2 | 10/2009 | Helmin et al. |
| 7,599,516 B2 | 10/2009 | Limer et al. |
| 7,606,723 B2 | 10/2009 | Mayaud |
| 7,610,115 B2 | 10/2009 | Rob et al. |
| 7,620,479 B2 | 11/2009 | Kircher et al. |
| 7,620,563 B2 | 11/2009 | Tornaquindici |
| 7,620,568 B1 | 11/2009 | Parker-Malchak |
| 7,631,475 B2 | 12/2009 | Baldwin et al. |
| 7,633,018 B2 | 12/2009 | Leisinger et al. |
| 7,636,718 B1 | 12/2009 | Steen et al. |
| 7,639,406 B1 | 12/2009 | Proudfoot et al. |
| 7,643,134 B2 | 1/2010 | Berndt |
| 7,651,664 B2 | 1/2010 | Appoldt et al. |
| 7,681,606 B2 | 3/2010 | Khan et al. |
| 7,689,465 B1 | 3/2010 | Shakes et al. |
| 7,698,019 B2 | 4/2010 | Moncrief et al. |
| 7,706,915 B2 | 4/2010 | Mohapatra et al. |
| 7,734,478 B2 | 6/2010 | Goodall et al. |
| 7,747,477 B1 | 6/2010 | Louie et al. |
| 7,753,085 B2 | 7/2010 | Tribble et al. |
| 7,765,108 B2 | 7/2010 | Goodall et al. |
| 7,769,221 B1 | 8/2010 | Shakes et al. |
| 7,771,659 B2 | 8/2010 | Ziegler |
| 7,801,642 B2 | 9/2010 | Ansari et al. |
| 7,814,731 B2 | 10/2010 | Bender et al. |
| 7,831,393 B2 | 11/2010 | Savva |
| 7,831,447 B2 | 11/2010 | Schuman |
| 7,837,103 B2 | 11/2010 | Suto |
| 7,845,551 B2 | 12/2010 | Helmin et al. |
| 7,847,970 B1 | 12/2010 | McGrady |
| 7,860,583 B2 | 12/2010 | Condurso et al. |
| 7,860,730 B1 | 12/2010 | Goodall et al. |
| 7,861,495 B2 | 1/2011 | Yuyama et al. |
| 7,873,435 B2 | 1/2011 | Yuyama et al. |
| 7,886,230 B2 | 2/2011 | Monnier et al. |
| 7,900,658 B2 | 3/2011 | Osborne et al. |
| 7,913,475 B2 | 3/2011 | Khan et al. |
| 7,913,720 B2 | 3/2011 | Tribble et al. |
| 7,917,329 B2 | 3/2011 | Hamamoto |
| 7,927,313 B2 | 4/2011 | Stewart et al. |
| 7,930,064 B2 | 4/2011 | Popovich, Jr. et al. |
| 7,930,066 B2 | 4/2011 | Eliuk et al. |
| 7,930,364 B2 | 4/2011 | Ramaswamy et al. |
| 7,937,290 B2 | 5/2011 | Bahir |
| 7,938,032 B2 | 5/2011 | Fernando |
| 7,941,915 B2 | 5/2011 | Yuyama et al. |
| 7,956,894 B2 | 6/2011 | Akers et al. |
| 7,964,805 B2 | 6/2011 | Yuyama et al. |
| 7,991,627 B2 | 8/2011 | Hutchinson et al. |
| 7,995,831 B2 | 8/2011 | Eller et al. |
| 8,024,913 B2 | 9/2011 | Khan et al. |
| 8,027,745 B1 | 9/2011 | Freeze |
| 8,029,941 B2 | 10/2011 | Zenitani et al. |
| 8,037,659 B2 | 10/2011 | Osborne et al. |
| 8,073,238 B2 | 12/2011 | Nakanishi et al. |
| 8,140,349 B2 | 3/2012 | Hanson et al. |
| 8,140,351 B2 | 3/2012 | Fribble et al. |
| 8,140,395 B2 | 3/2012 | Murphy et al. |
| 8,150,706 B2 | 4/2012 | Kobylevsky et al. |
| 8,151,835 B2 | 4/2012 | Khan et al. |
| 8,191,339 B2 | 6/2012 | Tribble et al. |
| 8,219,413 B2 | 7/2012 | Martinez et al. |
| 8,220,503 B2 | 7/2012 | Tribble et al. |
| 8,224,483 B1 | 7/2012 | Ansari et al. |
| 8,229,763 B2 | 7/2012 | Laughland et al. |
| 8,234,128 B2 | 7/2012 | Martucci et al. |
| 8,266,878 B2 | 9/2012 | Luciano, Jr. et al. |
| 8,280,549 B2 | 10/2012 | Liff et al. |
| 8,284,305 B2 | 10/2012 | Newcomb et al. |
| 8,295,582 B2 | 10/2012 | Eller et al. |
| 8,345,989 B1 | 1/2013 | Bresolin et al. |
| 8,353,318 B2 | 1/2013 | Ranalletta et al. |
| 8,374,887 B1 | 2/2013 | Alexander |
| 8,374,965 B2 | 2/2013 | Friend et al. |
| 8,417,539 B2 | 4/2013 | Chapman et al. |
| 8,433,129 B2 | 4/2013 | Nakanishi et al. |
| 8,442,298 B2 | 5/2013 | Nakanishi et al. |
| 8,448,846 B2 | 5/2013 | Needhan et al. |
| 8,463,622 B2 | 6/2013 | Garms et al. |
| 8,477,989 B2 | 7/2013 | Bresolin |
| 8,489,425 B2 | 7/2013 | Moncrief et al. |
| 8,554,579 B2 | 10/2013 | Tribble et al. |
| 8,555,206 B2 | 10/2013 | Pederson et al. |
| 8,571,297 B2 | 10/2013 | Eller et al. |
| 8,571,881 B2 | 10/2013 | Rousso et al. |
| 8,571,886 B2 | 10/2013 | Chudy et al. |
| 8,584,941 B2 | 11/2013 | Louie et al. |
| 8,678,047 B2 | 3/2014 | Tribble et al. |
| 8,682,042 B1 | 3/2014 | Manion et al. |
| 8,740,077 B2 | 6/2014 | Needham et al. |
| 8,763,651 B2 | 7/2014 | Stavsky et al. |
| 8,775,198 B2 | 7/2014 | Wiener et al. |
| 8,818,821 B2 | 8/2014 | Fioravanti |
| 8,869,297 B2 | 10/2014 | Hanov et al. |
| 8,881,980 B2 | 11/2014 | Magill |
| 8,908,163 B2 | 12/2014 | Young et al. |
| 9,053,616 B2 | 6/2015 | Grabiner et al. |
| 9,930,297 B2* | 3/2018 | Alexander ............ H04N 7/185 |
| 10,347,374 B2* | 7/2019 | Tribble ................ G16H 20/10 |
| 10,372,880 B2* | 8/2019 | Utech ................... G16H 20/10 |
| 10,554,937 B2* | 2/2020 | Alexander ............ H04N 7/185 |
| 11,064,164 B2* | 7/2021 | Alexander ............ A61B 90/96 |
| 2001/0042043 A1 | 11/2001 | Shear et al. |

(56) References Cited

U.S. PATENT DOCUMENTS

| | | |
|---|---|---|
| 2001/0048027 A1 | 12/2001 | Walsh |
| 2002/0049614 A1 | 4/2002 | Rice et al. |
| 2002/0057339 A1 | 5/2002 | Shoenfeld |
| 2002/0067411 A1 | 6/2002 | Thompson et al. |
| 2002/0071603 A1 | 6/2002 | Ungpiyakul et al. |
| 2002/0100762 A1 | 8/2002 | Liff et al. |
| 2002/0139394 A1 | 10/2002 | Bronson |
| 2002/0145042 A1 | 10/2002 | Knowles et al. |
| 2003/0021454 A1 | 1/2003 | Weyl |
| 2003/0041239 A1 | 2/2003 | Shear et al. |
| 2003/0050731 A1 | 3/2003 | Rosenblum |
| 2003/0074223 A1 | 4/2003 | Hickle et al. |
| 2003/0078849 A1 | 4/2003 | Snyder |
| 2003/0105555 A1 | 6/2003 | Lunak et al. |
| 2003/0107654 A1 | 6/2003 | Ohmura |
| 2003/0136590 A1 | 7/2003 | Gluvakov |
| 2003/0139701 A1 | 7/2003 | White et al. |
| 2003/0139706 A1 | 7/2003 | Gray |
| 2003/0140928 A1 | 7/2003 | Bui et al. |
| 2003/0144878 A1 | 7/2003 | Wilkes et al. |
| 2003/0158508 A1 | 8/2003 | DiGianfilippo et al. |
| 2003/0179287 A1 | 9/2003 | Kozic et al. |
| 2003/0195775 A1 | 10/2003 | Hampton et al. |
| 2003/0204357 A1 | 10/2003 | Hamilton |
| 2003/0225595 A1 | 12/2003 | Helmus et al. |
| 2004/0006494 A1 | 1/2004 | Badinelli |
| 2004/0017475 A1 | 1/2004 | Akers et al. |
| 2004/0019794 A1 | 1/2004 | Moradi et al. |
| 2004/0039481 A1 | 2/2004 | de la Huerga |
| 2004/0076318 A1 | 4/2004 | Faeldt et al. |
| 2004/0143459 A1 | 7/2004 | Engleson et al. |
| 2004/0150815 A1 | 8/2004 | Sones et al. |
| 2004/0172289 A1 | 9/2004 | Kozic et al. |
| 2004/0193454 A1 | 9/2004 | Foote et al. |
| 2004/0204954 A1 | 10/2004 | Lacko |
| 2004/0225528 A1 | 11/2004 | Brock |
| 2005/0055242 A1 | 3/2005 | Bello et al. |
| 2005/0080651 A1 | 4/2005 | Morrison et al. |
| 2005/0086008 A1 | 4/2005 | DiGianfilippo et al. |
| 2005/0125097 A1 | 6/2005 | Chudy et al. |
| 2005/0130173 A1 | 6/2005 | Leamon et al. |
| 2005/0133729 A1 | 6/2005 | Woodworth et al. |
| 2005/0197930 A1 | 9/2005 | Polarine |
| 2005/0240445 A1 | 10/2005 | Sutherland et al. |
| 2006/0041330 A1 | 2/2006 | Ansari et al. |
| 2006/0048841 A1 | 3/2006 | Luehrsen et al. |
| 2006/0059019 A1 | 3/2006 | Komischke et al. |
| 2006/0080041 A1 | 4/2006 | Anderson et al. |
| 2006/0080177 A1 | 4/2006 | Walter et al. |
| 2006/0088196 A1 | 4/2006 | Popovich, Jr. et al. |
| 2006/0106647 A1 | 5/2006 | Brummel et al. |
| 2006/0120588 A1 | 6/2006 | Kwon et al. |
| 2006/0136260 A1 | 6/2006 | Ash et al. |
| 2006/0136261 A1 | 6/2006 | Ash et al. |
| 2006/0136268 A1 | 6/2006 | Ash et al. |
| 2006/0173714 A1 | 8/2006 | Grotzinger, Jr. |
| 2006/0173896 A1 | 8/2006 | Lyon et al. |
| 2006/0178578 A1 | 8/2006 | Tribble et al. |
| 2006/0200369 A1 | 9/2006 | Batch et al. |
| 2006/0287884 A1 | 12/2006 | Sandy et al. |
| 2007/0021929 A1 | 1/2007 | Lemmo et al. |
| 2007/0043473 A1 | 2/2007 | Anderson et al. |
| 2007/0106425 A1 | 5/2007 | Anderson et al. |
| 2007/0114224 A1 | 5/2007 | Nagamitsu et al. |
| 2007/0156707 A1 | 7/2007 | Fuchs et al. |
| 2007/0162295 A1 | 7/2007 | Akhtar et al. |
| 2007/0189597 A1 | 8/2007 | Limer et al. |
| 2007/0228172 A1 | 10/2007 | Knowles et al. |
| 2007/0239482 A1 | 10/2007 | Finn et al. |
| 2007/0260491 A1 | 11/2007 | Palmer et al. |
| 2007/0265880 A1 | 11/2007 | Bartfeld et al. |
| 2007/0276867 A1 | 11/2007 | Fishbaine et al. |
| 2008/0045811 A1 | 2/2008 | Iliff |
| 2008/0047760 A1 | 2/2008 | Georgitsis |
| 2008/0052120 A1 | 2/2008 | Iliff |
| 2008/0052121 A1 | 2/2008 | Iliff |
| 2008/0052122 A1 | 2/2008 | Iliff |
| 2008/0052123 A1 | 2/2008 | Iliff |
| 2008/0052130 A1 | 2/2008 | Iliff |
| 2008/0052132 A1 | 2/2008 | Iliff |
| 2008/0056556 A1 | 3/2008 | Eller et al. |
| 2008/0059240 A1 | 3/2008 | Potuluri et al. |
| 2008/0086326 A1 | 4/2008 | Moura et al. |
| 2008/0105468 A1 | 5/2008 | Ragazzini et al. |
| 2008/0119958 A1 | 5/2008 | Bear et al. |
| 2008/0125897 A1 | 5/2008 | DiGianfilippo et al. |
| 2008/0195416 A1 | 8/2008 | Tribble et al. |
| 2008/0306761 A1 | 12/2008 | George et al. |
| 2008/0312861 A1 | 12/2008 | Casto et al. |
| 2009/0012818 A1 | 1/2009 | Rodgers |
| 2009/0030722 A1 | 1/2009 | Wiener et al. |
| 2009/0110019 A1 | 4/2009 | Houde-Walter et al. |
| 2009/0112179 A1 | 4/2009 | Zoltan et al. |
| 2009/0154764 A1 | 6/2009 | Khan et al. |
| 2009/0154789 A1 | 6/2009 | Wolfe |
| 2009/0198208 A1 | 8/2009 | Stavsky et al. |
| 2009/0202108 A1 | 8/2009 | Faeldt et al. |
| 2009/0204422 A1 | 8/2009 | James et al. |
| 2009/0265185 A1 | 10/2009 | Finn et al. |
| 2009/0323108 A1 | 12/2009 | Shimma |
| 2009/0326861 A1 | 12/2009 | Langford et al. |
| 2010/0042430 A1 | 2/2010 | Bartfeld |
| 2010/0057264 A1 | 3/2010 | Kircher et al. |
| 2010/0094653 A1 | 4/2010 | Tribble et al. |
| 2010/0293008 A1 | 11/2010 | Denny |
| 2010/0324936 A1 | 12/2010 | Vishnubhatla et al. |
| 2011/0029445 A1 | 2/2011 | Whittacre et al. |
| 2011/0031038 A1 | 2/2011 | Page |
| 2011/0184751 A1 | 7/2011 | Holmes |
| 2011/0202366 A1 | 8/2011 | Akers et al. |
| 2011/0234977 A1 | 9/2011 | Verdooner |
| 2011/0253693 A1 | 10/2011 | Lyons et al. |
| 2011/0307270 A1 | 12/2011 | Berkelhamer et al. |
| 2012/0185277 A1 | 7/2012 | Tribble et al. |
| 2012/0199239 A1 | 8/2012 | Okuda et al. |
| 2012/0330684 A1 | 12/2012 | Jacobs et al. |
| 2013/0088599 A1 | 4/2013 | Ulomek et al. |
| 2013/0194414 A1 | 8/2013 | Poirier et al. |
| 2014/0145082 A1 | 5/2014 | Fukuma |
| 2018/0091745 A1 | 3/2018 | Holmes |
| 2019/0290545 A1 | 9/2019 | Imai |

FOREIGN PATENT DOCUMENTS

| | | |
|---|---|---|
| EP | 1803431 A1 | 7/2007 |
| EP | 2323097 A1 | 5/2011 |
| EP | 2465483 A1 | 6/2012 |
| EP | 2465483 B1 | 6/2016 |
| GB | 2379037 A | 2/2003 |
| JP | 2000111450 A | 4/2000 |
| JP | 2005279228 A | 10/2005 |
| JP | 2006323505 A | 11/2006 |
| RU | 2009106403 A | 9/2010 |
| WO | 8700659 A1 | 1/1987 |
| WO | 9910029 A1 | 3/1999 |
| WO | 03040980 A1 | 5/2003 |
| WO | 03078112 A2 | 9/2003 |
| WO | 2005101279 A2 | 10/2005 |
| WO | 2006095850 A1 | 9/2006 |
| WO | 2007023829 A1 | 3/2007 |
| WO | 2008055194 A2 | 5/2008 |
| WO | 2008062485 A1 | 5/2008 |
| WO | 2011112606 A1 | 9/2011 |

OTHER PUBLICATIONS

Angaran, "Telemedicine and telepharmacy: Current status and future implications," American Journal of Health-System Pharmacy, Jul. 15, 1999, pp. 1521-1551, vol. 56, No. 14.

Anonymous, "Chains covet customized pharmacy integration," Drug Store News, Aug. 18, 2003, pp. 73, 74, 83, vol. 25, No. 10.

(56) References Cited

OTHER PUBLICATIONS

Bynum et al., "The Effect of Telepharmacy Counseling on Metered-Dose Inhaler Technique among Adolescents with Asthma in Rural Arkansas," Telemedicine Journal and e-Health, 2001, pp. 207-218, vol. 7, No. 3.
Cabral Jr. et al., "Multimedia Systems for Telemedicine and Their Communications Requirements," IEEE Communications Magazine, Jul. 1996, pp. 20-27.
Casey et al., "Access to Rural Pharmacy Services in Minnesota, North Dakota, and South Dakota," Working Paper Series, Jul. 2001, pp. 1-83, University of Minnesota Rural Health Research Center.
Casey et al., "Pharmacist Staffing and the Use of Technology in Small Rural Hospitals: Implications for Medication Safety," Upper Midwest Rural Health Research Center, Dec. 2005, pp. 1-51.
Clifton et al., "Provision of pharmacy services to underserved populations via remote dispensing and two-way videoconferencing," American Journal of Health-System Pharmacy, Dec. 15, 2003, pp. 2577-2582, vol. 60.
Dart, "Digital Doses: Telepharmacies save people in small towns and rural areas from having to drive hundreds of miles to fill a prescription," Rural Health Care, Jan. 2005, pp. 28-30.
Felkey, "Tools for Interactive Pharmacy," Computer talk for the pharmacist, Jan./Feb. 2001, pp. 43-45, vol. 21, Is. 1.
Felkey, "Integrating Technology at the Point of Care," Insight: The QS/1 Magazine, Jan. 2004, pp. 8-10.
Frady, "What's New in RxCare Plus 17.2," Insight: The QS/1 Magazine, Apr. 2002, p. 14.
Ghent, "Pharmacists go digital to fight shortage," Pharmacy Practice, Nov. 2004, p. 47, vol. 20, Is. 11.
Halverson, "Rural Wisconsin Health Cooperative: Virtual Private Network Feasibility and Design Study," Sep. 2001, pp. 1-49.
Hix, "Outpatient Pharmacies 'Booming': An Inside Look at Growth of an Industry," Insight: The QS/1 Magazine, Apr. 2004, pp. 15-17.
Hoerner, "Re: cytostatic programs," Pharmweb Internet Posting, Jan. 11, 1999, pp. 1-3.
"Improving after-hour pharmacy services for a community hospital by a remote pharmacy," Cardinal Health, 2003, pp. 1-3.
Kastango et al., "USP chapter 797: Establishing a practice standard for compounding sterile preparations in pharmacy," American Journal of Health-System Pharmacy, Sep. 15, 2004, pp. 1928-1938, vol. 61.
Keeys et al., "Providing nighttime pharmaceutical services through telepharmacy," American Journal of Health-System Pharmacy, Apr. 15, 2002, pp. 716-721, vol. 59.
Kosub, "Device allows pharmacy care in remote areas," Pharmacy Practice, Oct. 2004, pp. 12-13, vol. 20, No. 10, ProQuest.
Koutnik, "The Pharmacy of Tomorrow," Pharmacy Times, Aug. 1, 2003, pp. 1-3.
Langham, "Winston-Salem Health Care Pharmacy: Taking Automation to New Levels," Insight: QS/1 Magazine, Oct. 2002, pp. 4-5.
MacInnis et al., "Environmental Scan of Pharmacy Technicians," Canadian Pharmacists Association, Sep. 2001, pp. 1-16.
Morris et al., "National survey of quality assurance activities for pharmacy-compounded sterile preparations," American Journal of Health-System Pharmacy, Dec. 15, 2003, pp. 2567-2576, vol. 60.
Muller, "Electronic Prescribing: What You Need to Know!" Insight: QS/1 Magazine, pp. 11-12.
Muller, "Make Your Next Move: NRx, QS/1's Premium Pharmacy Software," Insight: QS/1 Magazine, Jul. 2003, pp. 13-15.
Napoli et al., "Picture archiving and communication in radiology," Rays, Jan.-Mar. 2003, (Abstract Only), pp. 1-2, vol. 28, No. 1, PubMed.
Nissen et al., "Can telepharmacy provide pharmacy services in the bush?" Journal of Telemedicine and Telecare, 2003, pp. 39-41, vol. 9, (Suppl. 2).
North Dakota State Board of Pharmacy Practice Act, 2003, pp. 1-219.
Notice of Allowance and Fee(s) Due from U.S. Appl. No. 11/056,511, filed Dec. 24, 2012, Emily H. Alexander, pp. 1-16.

Office Action from U.S. Appl. No. 11/056,511 dated Apr. 8, 2008, Emily H. Alexander, pp. 1-11.
Office Action from U.S. Appl. No. 11/056,511 dated Oct. 16, 2008, Emily H. Alexander, pp. 1-16.
Office Action from U.S. Appl. No. 11/056,511 dated Apr. 13, 2009, Emily H. Alexander, pp. 1-14.
Office Action from U.S. Appl. No. 11/056,511 dated Feb. 3, 2010, Emily H. Alexander, pp. 1-15.
Parks, "Annual report of retail pharmacy: Using central-fill to maximize dispensing," Drug Store News, Aug. 20, 2001, pp. 51, 75, vol. 23, No. 11, ProQuest Research Library.
Parks, "ATM-Style Drug Dispensers Taking Hold in Areas with Limited Pharmacist Services," Technology, Jan. 2004, pp. 1-6, vol. 31, No. 1.
Peterson et al., "Telepharmacy," Telemedicine Technical Assistance Documents: A Guide to Getting Started in Telemedicine, pp. 206-400.
Petition for Inter Partes Review of U.S. Pat. No. 8,374,887, pp. 1-69.
"Pharmaceutical Compounding—Sterile Preparations," United States Pharmacopeia, Jan. 1, 2004, pp. 2350-2370.
Phillips, "Telepharmacy at Texas Tech," pp. 1-26.
Reference Manual for Computer Aided Therapy for Oncology (CATO), May 2005, pp. 1-255.
"Regulatory Compliance News Summary now includes global pharmaceutical regulatory news," First Consulting Group, Aug. 24, 2004, pp. 1-7.
Rouse, "White paper on pharmacy technicians 2002: Needed changes can no longer wait," American Journal of Health-System Pharmacy, Jan. 1, 2003, pp. 37-51, vol. 60.
"Rural Hospital Joins the Big Leagues with the Power of a Kodak PACS/Enterprise Information Management (EIM) Solution," Kodak Medical Systems, pp. 1-4.
Scheraga, "Pharmacy Automation: Tech firms answer chain pharmacy's call for productivity," Drug Store News, Dec. 15, 2003, pp. 31-32.
"SP 200 with Collating Control Center Robotic Prescription Dispensing System," ScriptPro, p. 1.
"SP 200: Robotic Prescription Dispensing System," ScriptPro, p. 1.
"SP Automation Center 200TM (SPace 200TM) Prescription Dispensing Automation Center," ScriptPro, p. 1.
Seifert et al., "The Training of a Telepharmacist: Addressing the Needs of Rural West Texas," American Journal of Pharmaceutical Education, Jul. 16, 2004, pp. 1-9, vol. 68, No. 3.
Tracy et al., "Telemedicine Technical Assistance Documents: A Guide to Getting Started in Telemedicine," 2004, pp. 1-400.
Title 22, Part 15, Chapter 291, Rules 20, 36, and 71-74 of the Texas Administrative Code, Feb. 10, 2004, pp. 1-70.
Ukens, "Pharmacist shortage boosts telepharmacy," Drug Topics, Jun. 3, 2002, p. 53, vol. 146, No. 11.
U.S. Appl. No. 11/056,511, filed Feb. 11, 2005, Emily H. Alexander, pp. 1-40.
Wills, "Drug Images and Drug Imprints: Delivering Tools for Accuracy in Your Pharmacy," Insight: The QS/1 Magazine, Apr. 2004, p. 7.
Woodall, "Remote Order Entry and Video Verification: Reducing After-Hours Medication Errors in a Rural Hospital," Joint Commission Journal on Quality and Safety, Aug. 2004, pp. 442-447, vol. 30, No. 8.
Yahoo Mail, Oct. 11, 2008, pp. 1-2.
Young, "Loan repayments help pharmacists provide care in medically underserved areas," American Journal of Health-System Pharmacy, Nov. 1, 2003, pp. 2186-2188, vol. 60.
Inguanti, "The IntelliFill i.v. from ForHealth Technologies, Inc.," Product Spotlight, Oct. 2006, p. 22.
Cote et al., "Robotic system i.v. antineoplastic drug preparation:Description and preliminary evaluation under simulated conditions", American Journal of Hospital Pharmacy, 1989, pp. 2286-2293, vol. 46.
O'Neal et al., "Telepharmacy and bar-code technology in an i.v. chemotherapy admixture area", Am J Health-Syst Pharm, 2009, pp. 1211-1217, vol. 66.

(56) References Cited

OTHER PUBLICATIONS

Young, "Telepharmacy project aids North Dakota's rural communities", Am J Health-Syst Pharm, 2006, pp. 1776-1780, vol. 63.

* cited by examiner

SYSTEM AND METHOD FOR ACQUIRING IMAGES OF MEDICATION PREPARATIONS

CROSS-REFERENCE TO RELATED APPLICATIONS

This application is a continuation of U.S. patent application Ser. No. 16/725,084 entitled "System and Method for Acquiring Images of Medication Preparations", filed Dec. 23, 2019, which is a continuation of U.S. patent application Ser. No. 15/895,377 entitled "System and Method for Acquiring Images of Medication Preparations", filed Feb. 13, 2018 (now U.S. Pat. No. 10,554,937), which is a continuation of U.S. patent application Ser. No. 13/097,575 entitled "System and Method for Acquiring Images of Medication Preparations", filed Apr. 29, 2011 (now U.S. Pat. No. 9,930,297), which claims priority to U.S. Provisional Patent Application No. 61/330,146 titled "System and Method for Acquiring Images of Medication Preparations", filed Apr. 30, 2010, the contents of which are hereby incorporated by reference in their entirety.

BACKGROUND

Field

The present disclosure relates to pharmacy services, and more specifically, to a method and a system for acquiring and using images of preparations of substances. More particularly, the present disclosure relates to acquiring and using images of medication preparations.

Description of the Related Art

A pharmacist's scope of practice in institutions, such as hospitals, or correctional facilities, includes preparing, packaging, compounding, and labeling medication, compounding sterile products, as well as other medication related activities. Many technical functions involving the preparation and distribution of drugs may be performed in the institution by non-pharmacist personnel, usually a pharmacy technician, licensed nurse, pharmacy student, pharmacy intern, nursing student or trainee, or a pharmacy technician student or trainee. When a non-pharmacist (such as a technician) performs such functions, or when a pharmacist performs such functions involving high cost and/or high risk medications, a pharmacist must generally verify their work.

When technical pharmacy functions are performed (whether by a pharmacist, or a non-pharmacist, such as a nurse), a pharmacist typically verifies the work, in part, by comparing it to either a copy of the original medication order, or a medication order previously entered into the patient's medication profile. The pharmacist also supervises the work of the non-pharmacist, and verifies that the medication product has been correctly and accurately prepared, labeled, compounded, and/or packaged. When a non-pharmacist performs technical pharmacy functions involving prepackaging, labeling, bulk compounding, or batch preparation of medications that will serve as stock medication in the pharmacy department, a pharmacist must generally verify the work in much the same manner. The pharmacist must supervise the work of the non-pharmacist to verify that the medication has been correctly and accurately prepared, labeled, compounded, and/or packaged.

Preparation of medications typically involves several steps. Typically, a medication order, such as an order for a prescription drug or stock requisition, is delivered to a technician. The technician prepares the medication based on the specifications of the order, and according to an established protocol. The technician's work in preparing the medication is supervised and approved by a pharmacist.

Direct and personal oversight and approval by a pharmacist for preparation of medications is typically required, for example, under pharmacy laws and regulations of various states. In some cases, however, the pharmacist may not be at the facility where preparation of the medication occurs, or may be in the facility but not in an area enabling physically present direct supervision of the preparation of the medication. In such cases, approval may sometimes be carried out through the transmission or exchange of information such as photographs of the preparation at various stages and/or videoconferencing between the technician and the pharmacist.

Some preparation facilities have a camera that can be used to take photographs of various stages in the preparation of a medication. Image data from the camera may be transmitted (for example, over a computer network) to a remote location where the supervising pharmacist is. At the remote location, the pharmacist may use the photographs to monitor the preparation of the medication and notify the technician of the pharmacist's approval. Many existing cameras, however, are not suitable for a sterile medical environment. For example, many cameras have bases, stands, tripods, platforms, cables, or exterior surfaces of the camera that cannot be effectively sterilized without damaging the camera or related equipment. In addition, positioning the camera and managing the image data produced by the camera may be cumbersome and time-consuming, especially in facilities where multiple preparations are occurring at the same time.

Managing workflow and keeping track of the photographic data may also be difficult for technicians working with an off-site pharmacist, especially when multiple preparations are occurring simultaneously at the same preparation facility, or when one remote pharmacist is overseeing many preparations at more than one preparation facility.

SUMMARY

Systems and methods are described herein for acquiring and using images of preparations, such as medication preparations. According to one embodiment, a system for holding a camera for acquiring images of preparations includes a rail that can be mounted above a preparation surface. A camera carrier couples a camera with the rail such that the camera is movable relative to the rail and such that the camera can acquire images of preparations on the preparation surface. In some embodiments, the surface and the camera carrier are in a sterile environment. In certain embodiments, the system is mounted in a hood.

According to one embodiment, a system for holding a camera for acquiring images of preparations includes a camera carrier that holds the camera above a preparation surface. A camera case houses the camera and protects the camera during cleaning of the workstation. A wireless device may transmit information between the camera and one or more computer systems.

According to one embodiment, a system for acquiring images of preparations includes a camera and a wireless transmitter. The wireless transmitter sends information from the camera to a computer system. User-operated triggers external to the camera can be used to control one or more functions of the camera (such as taking photos). In some embodiments, external manual triggers are provided on a case that can be wiped down during cleaning of a workstation.

According to one embodiment, a method of acquiring images of preparations includes capturing, with an image capture device, one or more images of at least one stage of a first preparation at a first zone. The image capturing device may be moved to point at a second zone. Images may be captured of at least one stage of a second preparation at the second zone. In some embodiments, a sterile environment is created and maintained in the zones during the making of the preparations.

According to one embodiment, a method of acquiring images of preparations includes placing an identifier code (such as a semacode) with a preparation. Images are captured of at least one stage of the preparation. The identifier code is visible in the images. The identifier code is automatically read from the images. The identifier code in the image is used in the evaluation of the preparation (such as by associating all the images for the preparation with one another based on the identifier code, or prioritizing the preparation over preparations having other identifier codes). In some embodiments, the order of workflow may be based on the identifier codes for different preparations.

According to one embodiment, a method of making a preparation includes placing a preparation identifier code (such as a semacode) with the preparation. In addition, identifier codes (such as a one-dimensional ("1D") barcode) on the ingredients are also visible in the work area. Images are captured of at least one stage of the preparation. The preparation identifier code and the ingredient identifier codes are visible in the images. The identifier codes are automatically read from the images. The identifier codes in the image are used to verify that the correct ingredients are being used for the preparation. If the correct ingredients are not used, a warning device can warn one or more participants involved in preparing the medication.

Figure 1:
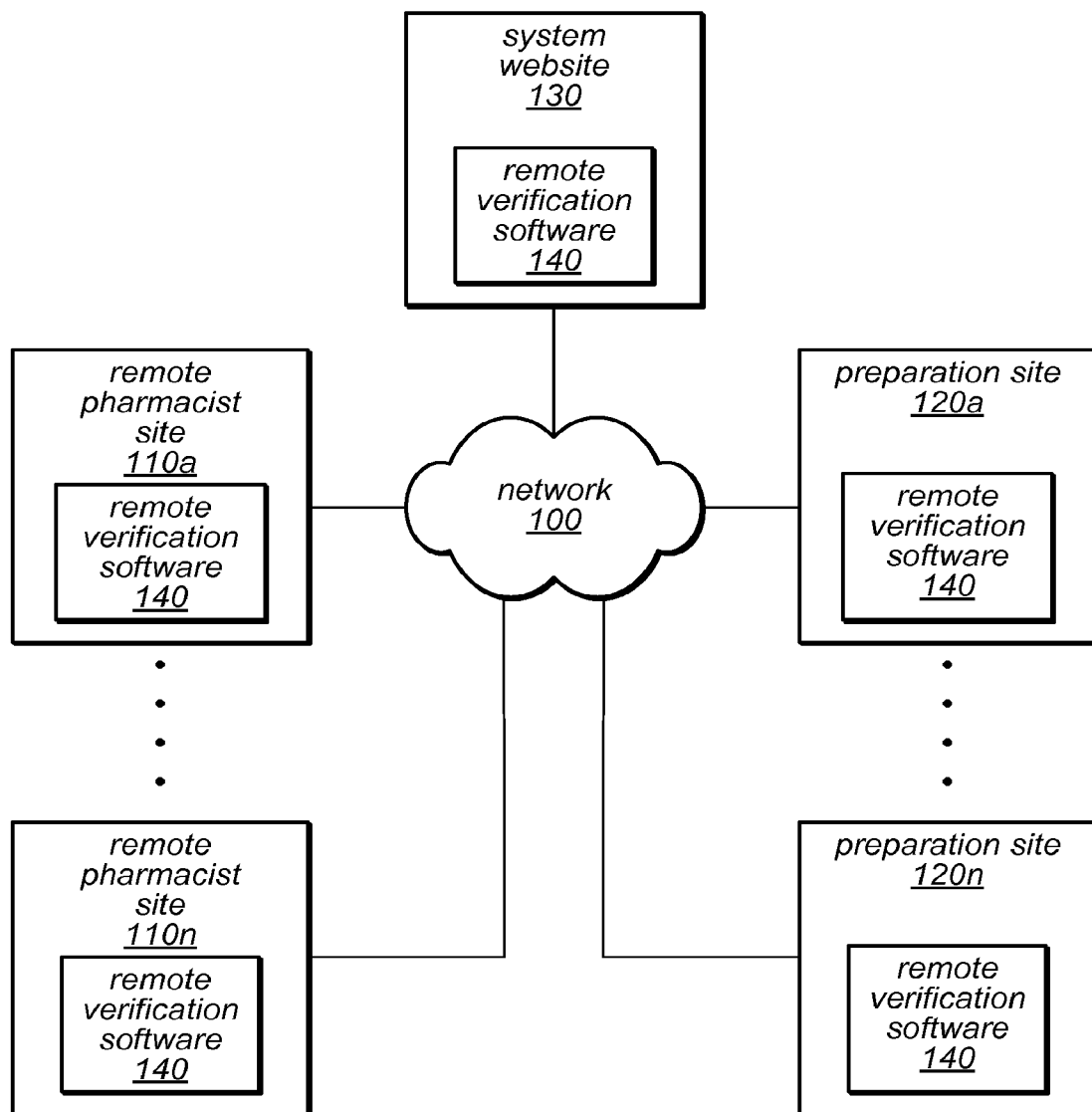
FIG. 1 illustrates a block diagram of one embodiment of a networked environment suitable for implementing remote supervision and verification of pharmacy functions.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

As used herein, a "preparation site" includes any facility, room, space, or location that can be used to make preparations. In some embodiments, a preparation site is an institutional pharmacy, such as a pharmacy at a hospital or a correctional facility. In various embodiments, a preparation site may be at an educational facility (such as a pharmacy school), a clinic (such as an outpatient clinic), a laboratory (such as a lab in a teaching facility), a nursing floor in a hospital, or other location. In some embodiments, a preparation site is in a sterile environment. In other embodiments, a preparation site is in a non-sterile environment.

As used herein, a "workstation" includes any station, system, apparatus, space, facility, or combination thereof at which medications or medication orders and/or requisitions can be prepared or chemical mixing procedures can be performed. In some embodiments, a workstation may allow for multiple preparations to be prepared simultaneously. In some embodiments, a workstation may have two or more substations at which medications can be prepared. A workstation may accommodate activities by more than one worker at a time.

As used herein, "medication" means any chemical, composition, or combination thereof, that can be used for treatment, diagnosis, or prevention of disease. A medication may be, for example, a drug capsule that is to be taken by a patient, such as an antibiotic or chemotherapy drug.

As used herein, "chemical mixing procedure" means any procedure that includes mixing, dissolving, or otherwise combining chemicals, compositions, or materials. A chemical mixing procedure may include, for example, the mixing of compositions for pharmaceutical applications, such as in the making of prescription drugs.

As used herein, "image" includes a still image (such as a still photograph), a moving image or images (such as video), and combinations thereof. As used herein, a camera includes any device or combination of devices that can capture images. A camera may be a still camera or a videocamera.

As used herein, a "rail" includes any member that allows another element to slide or translate along its length. A rail may have various forms including a rod, a bar, a beam, or a plate. A rail may be straight, curved, or a combination thereof. A rail may have any cross section, including round, square, rectangular, ovate, or irregular. The cross section of a rail may vary over the length of the rail.

As used herein, a "hood" includes any enclosure or partial enclosure that at least partially inhibits contamination in at least a portion of a work area or that contains fumes or liquids from a chemical mixing procedure.

As used herein, "clean zone" means a space or area that is kept clean for purposes of making preparations. A clean zone may include one or more barriers for keeping contaminants out of the zone. In some embodiments, a clean zone is the interior of a hood. In some embodiments, a clean zone is periodically cleaned or sterilized. As used herein, "clean zone" does not require that an area be entirely free of contaminants.

As used herein, "sterile environment" includes an environment in which biological and particular matter are filtered or excluded within acceptable limits.

As used herein, "target zone" means an area where an imaging device is pointed. A target location may be, for example, a portion of the top surface of a table at which a camera is aimed.

As used herein, a "table" includes any structure or element having a surface on which medications can be prepared or chemical mixing procedures can be carried out. A table may have legs or other supports for holding the working surface. A table may supported by another structure, such as an adjacent wall.

As used herein, "target indicating device" includes any device that provides an indication of a target zone of a camera. A target indicating device may, for example, be a projection device, such as a laser pointer, that projects a frame onto the surface of a table. The image actually taken by a camera may vary from the indicators provided by the target indicating device. For example, a target indicating device may project a frame that is smaller than the image actually taken by a camera.

As used herein, "trigger" includes any element or device that causes something to happen, such as activating, switching, or releasing a device. For example, a trigger may activate a shutter on a camera. As another example, a trigger may change the state of a switch (such as on/off) or change a setting on a device. A trigger may include various devices, including an electronic switch, a push button, a lever, a thumbwheel, or a knob. A trigger may work in combination with other elements, such as levers, cables, wheels, gears, rods, cams, or other members. In certain embodiments, a trigger may be implemented through a command from a computer system. In certain embodiments, a trigger may be automatic.

Pharmacy functions (which may be performed by a pharmacist, or by a non-pharmacist such as a technician, nurse, pharmacy intern, or a student) may be remotely supervised and verified by a remote pharmacist using a networked environment, such as illustrated by FIG. 1, according to some embodiments. Pharmacists at one or more remote pharmacist sites 110 may remotely supervise and verify pharmacy work tasks performed by personnel at one or more preparation sites 120, according to some embodiments. Remotely supervised and verified pharmacy work tasks may include pharmacy functions performed pursuant to medication orders and may also include pharmacy functions not related to specific medication orders, according to various embodiments. In general, the term "pharmacy work task" as used herein may describe any pharmacy functions capable of being remotely supervised and verified by the methods and systems described herein, whether or not performed pursuant to a medication order.

As illustrated in FIG. 1, a remote pharmacist site may be linked to one or more preparation sites while located remotely from the preparation sites. For instance, preparation site 120 and remote pharmacist site 110 may be located in different parts of the same building, in one embodiment. In other embodiments, however, preparation site 120 and remote pharmacist site 110 may be in different buildings of the same institution, in the same town, in different cities, counties, or states. In general, remote pharmacist site 110 and preparation site 120 may be located anywhere as long they can communicate with each other either directly or indirectly.

Remote pharmacist site 110 and preparation site 120 may communicate via any of various wired or wireless communication systems, according to various embodiments. For example, in one embodiment, they may communicate via email over the Internet. In another embodiment, they may communicate via a custom communication protocol configured for exchanging messages related to remotely supervising and verifying pharmacy functions, such as may be implemented by remote verification software 140, as will be discussed herein below. In yet another embodiment, remote pharmacist site 110 and preparation site 120 may communicate via a website or electronic bulletin board, such as system website 130, by uploading and downloading various documents, images and/or other information related to remotely supervising and verifying pharmacy functions. Additionally, remote pharmacist site 110 may communicate with a pharmacy order entry system or other software at preparation site 120 via an Internet connection, virtual private network, or any wired or wireless link, according to one embodiment. For example, a pharmacist at remote pharmacist site 110 may communicate with such an order entry system or other software at preparation site 120 in order to verify a patient's medication order.

As illustrated by FIG. 1, multiple remote pharmacist sites 110 may exist in the system at once, as well as multiple preparation sites 120, according to some embodiments. A single remote pharmacist 110 may remotely supervise and verify pharmacy functions performed at more than one preparation sites 120. Additionally, a pool of remote pharmacist sites 110 may work together to remotely supervise and verify pharmacy functions performed at multiple preparation sites 120, in some embodiments. For example, a number of remote pharmacist sites 110 may each remotely supervise and verify pharmacy functions for any of a number of preparation sites 120 on a rotational or as needed basis. For instance, in one embodiment, a pharmacist at remote pharmacist site 110 may check and/or verify images from one or more preparation sites 120 randomly chosen out of a number of available preparation sites 120. In another embodiment, a remote pharmacist site may remotely verify pharmacy functions performed at a number of preparation sites on a first-come first-served basis in which the preparation sites are serviced in the order they notified the remote pharmacist that images were available for verification.

According to some embodiments, pharmacy functions performed at preparation site 120 that may be remotely supervised and verified may include, but are not limited to:
1. Packaging, prepackaging and labeling unit and multiple dose packages.
2. Medication preparation, packaging, compounding or labeling pursuant to medication orders.
3. Compounding of sterile pharmaceuticals pursuant to medication orders.
4. Bulk compounding or batch preparation.

The terms prepackaging and packaging, as used herein, may refer to two different pharmacy functions. Prepackaging refers to the re-packaging and/or re-labeling quantities of drug products from a manufacturer's original commercial container, such as into a prescription container for dispensing. Packaging, on the other hand, refers to collecting one or more medications into a final package to be dispensed to the ultimate consumer. For example, packaging may refer to a technician selecting appropriate quantities of manufacturer's unit dosed products and/or prepackaged stocked medications necessary to fill a patient's admission orders. The technician may then package the selected medications into a bag with an affixed label indicating the patient for whom the medications were ordered. As with other pharmacy functions, the prepackaging and the final packaging of medications may be remotely supervised and verified by a pharmacist, as described herein.

Remote verification of pharmacy functions performed by non-pharmacists may additionally include, in some embodiments, one or more legally required in-progress checks. In general, remote pharmacist verification of pharmacy work performed by non-pharmacists may include supervision and/or verification of the pharmacy work in various stages of completion as well as verification of any and/or all results of the pharmacy work, according to various embodiments.

A preparation site 120 may be a pharmacy located in an institution, such as a hospital or correctional facility. In general, preparation site 120 may be any pharmacy that cannot or does not have a pharmacist on site at all times. As illustrated in FIG. 1, preparation site 120 may be linked to a system website 130 and/or one or more remote pharmacist site(s) 110 via any of a number of ways, such as over the Internet, a virtual private network, or, in general, any wired or wireless communication system configured to allow the exchange of information related to remote supervision and verification of pharmacy functions, as described herein. For instance, preparation site 120 may communicate with remote pharmacist site 110 over network 100, which may be the Internet in one embodiment. In other embodiments, preparation site 120 may communicate with remote pharmacist site 110 directly over a telecommunications system, such as the Public Switched Telephone Network (PSTN) or over a cellular or satellite telecommunications system.

In some embodiments, system website 130 may represent an electronic bulletin board, or other shared electronic data storage facility, to which images, documents, and/or other files may be posted, uploaded, or otherwise stored. Images uploaded or posted to a web site or bulletin board may be compressed, encrypted, or combined (either compressed or uncompressed) into a single file, according to various embodiments. For example, in one embodiment, captured images may be uploaded in an encrypted form and a key or password to decrypt the images may be provided to a remote pharmacist in a separate communication. Furthermore, system website 130 may require secure login credentials, such as a username and password, before allowing images to be uploaded or accessed. Alternatively, a public/private key encryption schema may be utilized to ensure the security of the captured images in some embodiments. For example, the captured images may be encrypted using the remote pharmacist's public encryption key and may be decrypted by the pharmacist using the pharmacist's private encryption key. Additionally, any of various forms of secure electronic communication may be utilized to transfer the captured images in some embodiments. For example, in one embodiment, one or more images of pharmacy work may be transferred to system website 130 via a secure http protocol, such as HTTPS. In yet other embodiments, captured images may be digitally signed using digital certificate technology. For instance, the images may be digitally signed using the preparations site's digital signature or certification which a remote pharmacist may verify using an appropriate digital certification authentication authority. As encryption, secure electronic communication, and digital signature and certificate technologies are well understood in the art, they are not discussed in detail herein.

When personnel, such as pharmacy technicians, licensed nurses, pharmacy students, pharmacy interns, nursing students or trainees, and/or pharmacy technician students or trainees perform pharmacy functions requiring the supervision and verification of a pharmacist, (for example, in the absence of an on-site pharmacist), a still image capture device can be used to capture one or more images of the pharmacy work performed. The captured images may, in some embodiments, include images of all work and documentation required to properly supervise and verify the correct and accurate preparation, labeling, compounding, prepackaging and/or packaging, of any pharmacy work performed. The captured images may also include any additional documentation required for record keeping purposes, in some embodiments. In some embodiments, the captured images, exchange messages, and related documentation are compiled and stored as a permanent record for a preparation. Multiple images may be captured for remote supervision and verification process as needed, according to some embodiments. For example, if all documentation and materials required for the pharmacy work do not fit in the view of an image capture device, two or more images may be captured.

Preparation Workstation

In some embodiments, a preparation site, such as a pharmacy, includes one or more preparation workstations. A preparation workstation may be used to implement remote supervision and verification of pharmacy functions, as described herein. In some embodiments, a workstation area is in a sterile environment.

As discussed above, a supervising pharmacist may, in some cases, be in a separate location from the preparation workstation. In some cases, however, a supervising pharmacist may be at the same facility, but in a non-sterile part of the facility (for example, in the room next door to a lab where the workstation is located). Thus, for example, a pharmacy technician student may make medication preparations in a sterile environment while a pharmacist supervises the preparation in a non-sterile environment. Allowing the pharmacist to be in a non-sterile environment may relieve the pharmacist of having to take special precautions to maintain a sterile environment.

In some embodiments, an image capture device is suspended above a work area for preparations. Suspending an image capture device above a work area may eliminate some components that may be difficult to sterilize effectively (such as the legs of a tripod or base for a camera).

Figure 2:
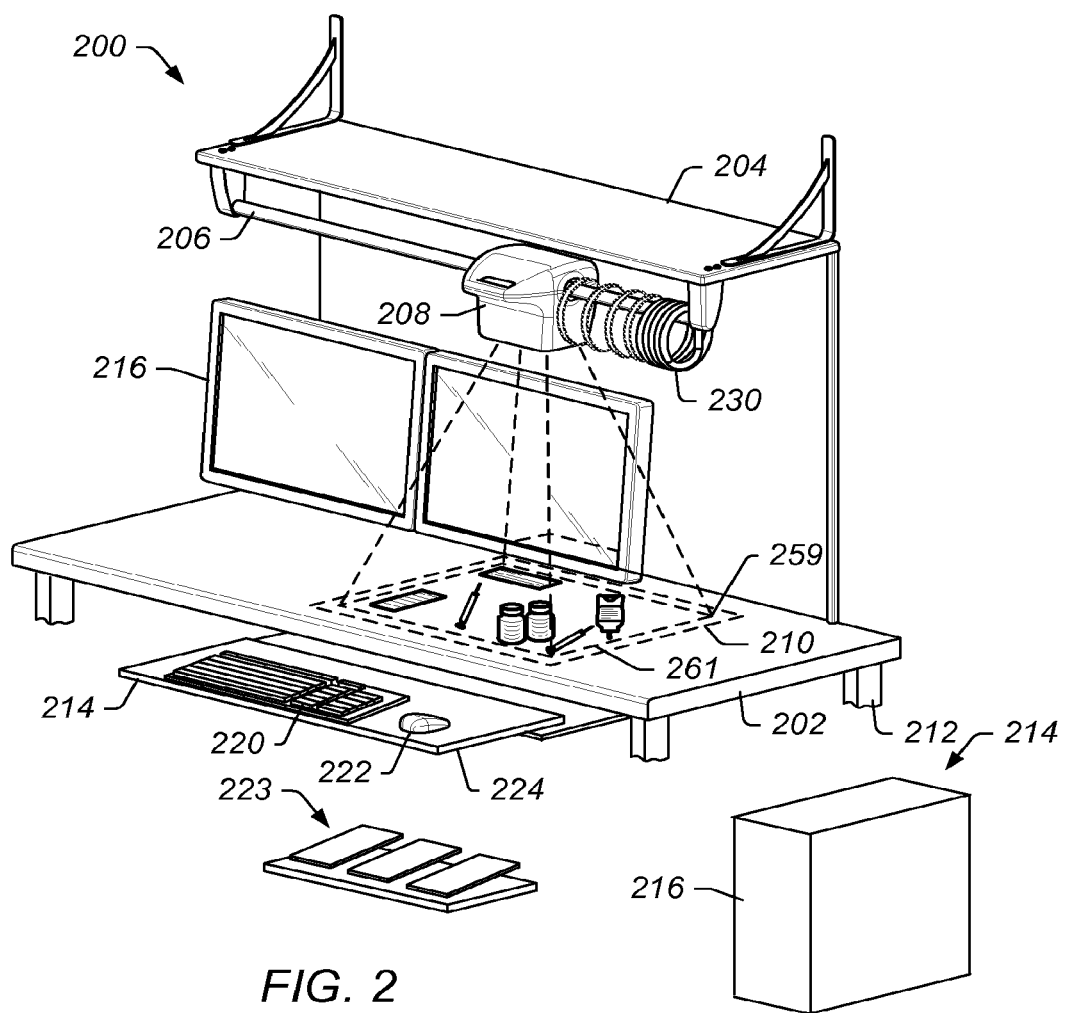
FIG. 2 illustrates one embodiment of a workstation including a movable image capture device.

FIG. 2 illustrates one embodiment of a preparation workstation including a movable image capture device. Workstation 200 includes table 202, rail support assembly 204, rail 206, and camera assembly 208. Rail support assembly may be coupled to table 202. Rail support assembly 204 supports rail 206. Camera assembly 208 may slide along rail 206. Camera assembly 208 may include a camera that is aimed downwardly toward table 202. The camera may acquire images of objects on table 202. The images acquired by the camera may include, for example, still images, short video clips, or live video feeds, or combinations thereof. For example, with the camera assembly positioned as shown in FIG. 2, the camera may acquire images of objects that are within zone 210 on table 202. As camera assembly 208 translates to the left or to the right on rail 206, the target zone of the camera may move correspondingly to the left or to the right. Thus, camera assembly 208 can be positioned to capture images in different areas on table 202.

Table 202, as well as the other components of workstation 200, may be supported on legs 212. Elements of a workstation may, however, be supported in any suitable manner. For example, a rail support assembly and/or table for a workstation may be mounted on a wall. In other embodiments, a workstation may be free-standing. In one embodiment, a workstation may be supported on a countertop. In certain embodiments, elements of a workstation may be supported on a rolling cart.

Workstation 200 includes computer system 214. Computer system 214 may include processing unit 216, monitors 218, keyboard 220, mouse 222, and foot pedal switch 223. In certain embodiments, a workstation includes a hand-operated switch in addition to, or instead of, foot pedal switch 223. Keyboard 220 and mouse 222 may rest on tray 224. The various components of computer system 214 may be connected to processing unit 216 by cables (for clarity, cables are not shown in FIG. 2) or by wireless connections. In certain embodiments, a workstation may include a printer, scanner, telephone, facsimile machine, and various other peripheral devices. Foot pedal switch 223 may be coupled to computer system 214, camera assembly 208, or both. Foot pedal switch may be operable by a user to control functions in camera assembly 208 or related to preparations (for example, uploading images acquired using camera assembly 208 to a pharmacist on a remote computer system).

Electrical devices in camera assembly 208 may be coupled to computer system 214 and/or other systems. Camera assembly 208 may be connected by way of cables that are carried in cable routing 230. In some embodiments, cables in cable routing 230 may carry signals, data, and/or power. Cable routing 230 may uncoil as necessary depending on the position of camera assembly 208 along rail 206.

Figure 2A:
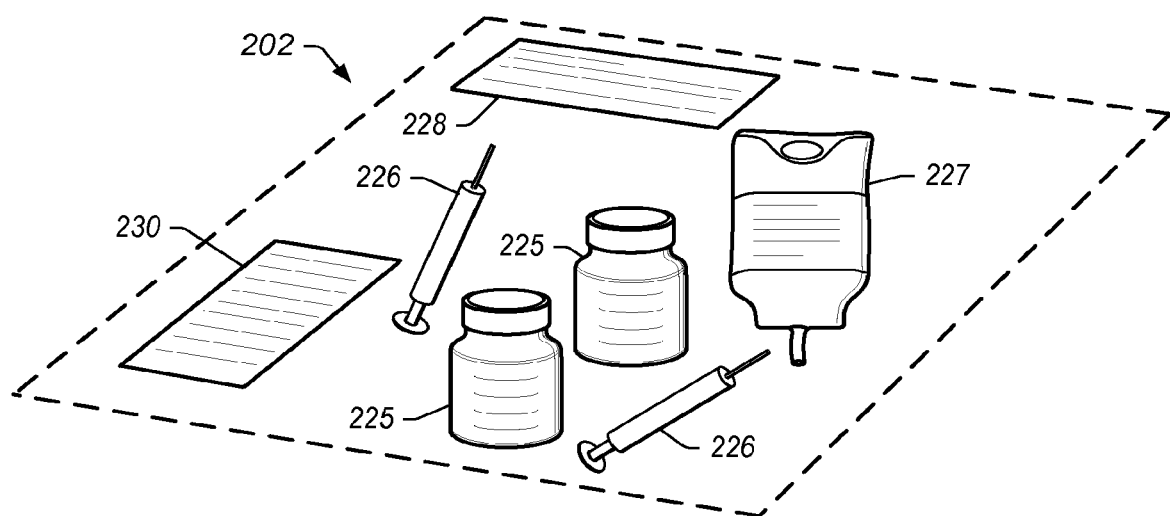
FIG. 2A is a detail view illustrating elements that can be captured in an image of pharmacy work for remote supervision and verification, according to one embodiment.

FIG. 2A is a detail view illustrating elements that can be captured in an image of pharmacy work for remote supervision and verification, according to one embodiment, Some or all of the elements may have a barcode on them. The barcode may be, for example, part of their packaging, or added to the elements. When a non-pharmacist worker produces pharmacy work, such as pursuant to a medication order or other pharmacy work task, one or more images of the pharmacy functions performed may be captured by an image capture device, such as camera assembly 208. For instance, after performing a pharmacy function requiring supervision and verification by a pharmacist, the non-pharmacist worker may move the job to a position at the workstation so that all materials and documentation required to properly supervise and verify correct and accurate preparation, labeling, compounding, prepackaging and/or packaging performed during the pharmacy functions are captured in by the image capture device. For example, in one embodiment, a non-pharmacy worker may perform one or more pharmacy functions and may capture images of the materials used, such as medicine vials 225, syringes 226, intravenous product 227, and documentation 228 and 230, as illustrated in FIG. 2A. In some embodiments, several images may be captured as the work is performed, each capturing a different stage of the pharmacy work being performed. Additionally, one or more images may be captured of the completed work. In some embodiments, the worker may move and display the materials and documentation for image capture, while in other embodiments, images may be captured of the materials and documentation in place as they are used during the performance of pharmacy functions.

In some embodiments, making and evaluating preparations may include creating and maintaining a sterile environment. A workstation may in some embodiments include a sterile environment. In some embodiments, a workstation includes a hood. The hood may avoid contamination of preparations at the workstation. Technicians and other personnel at or near the workstation may wear gloves, masks, head covering, and clothing that are sterile and suitable for use in a sterile environment.

Figure 3:
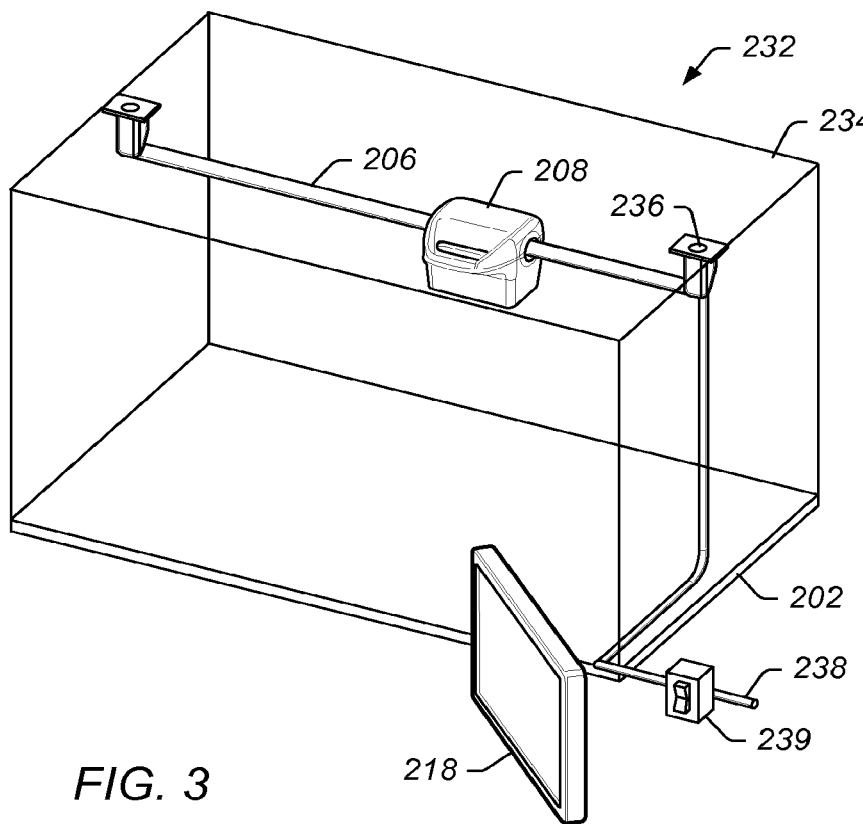
FIG. 3 illustrates one embodiment of a workstation including a hood.

FIG. 3 illustrates one embodiment of a workstation including a hood. Workstation 232 includes table 202, hood 234, and mounting brackets 236. Rail mounting brackets 236 may be coupled to the upper wall of hood 234. In some embodiments, rail mounting brackets 236 couple to existing mounting hardware in a hood. In certain embodiments, a rail mounting brackets 236 are designed to fit to existing mounting hardware in a variety of hoods (for example, standard, commercially available hoods). Rail mounting brackets 236 may carry rail 206. Camera assembly 208 may move along rail 206. Power cable 238 may supply power to camera assembly 208. In some embodiments, power is carried from cable 238 to camera assembly 208 through conductors in rail 206. Power switch 239 may be provided on power cable 238. Power switch 239 may be manually operated by a user to turn power to camera assembly 208 on and off. In certain embodiments, power conductors to the rail may be routed through the end of the rail (for example, through sealed contacts in the bracket at the end of the rail), such that there are no power cables or wires exposed in the hood. Having power transmitted through a rail, rather than cables routed externally to the rail, may make cleaning procedures in the hood easier and more effective. In certain embodiments, a transmission system may transmit signals or data by way of rail conductors, in addition to, or instead of, transmitting electrical power.

In some embodiments, power cable 238 consists of a flat electrical cable. The electrical cable may be sandwiched between two layers of PVC Tape. The electrical cable can also be routed in-between a sealing gasket and sealing surface to provide power without compromising the hood's sterile environment. In certain embodiments, the electrical cable is adhered to the hood wall, which may facilitate cleaning.

Figure 4:
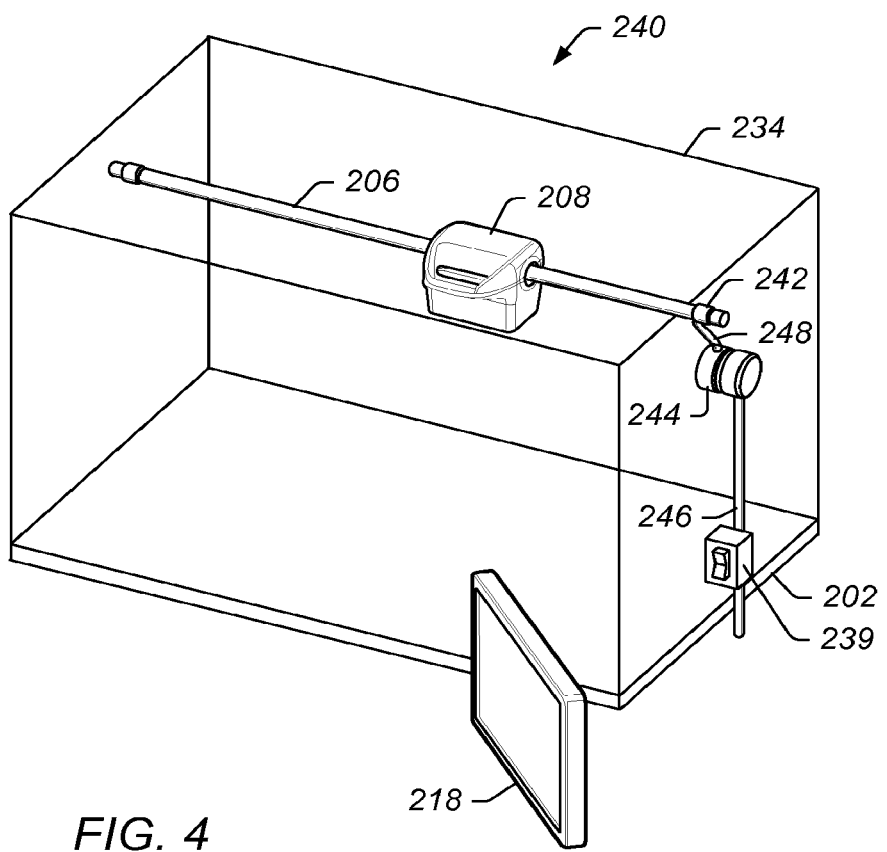
FIG. 4 illustrates an embodiment of a workstation having inductive coupling for transmitting power through a hood.

In some embodiments, electrical power is transmitted into the interior of a hood without any openings in the hood. FIG. 4 illustrates an embodiment of a workstation having inductive coupling for transmitting power through a hood. Workstation 240 includes table 202, hood 234, mounting brackets 242, and inductive coupling device 244. Rail mounting brackets 242 may mount to hood 234. Mounting brackets 242 may support rail 206. Camera assembly 208 may move along rail 206.

One half of inductive coupling device 244 is mounted on each side of a wall 247 of hood 204. Inductive coupling device 244 may transmit power to electrical devices in camera assembly 208. Cable 246 may carry conductors that transmit power from outside hood 234 to inductive coupling device 244. Cable 248 may include conductors that transmit power between inductive coupling device 244 and rail 206. In certain embodiments, an inductive coupling may carry data and/or signals to and/or from a camera assembly.

Figure 5:
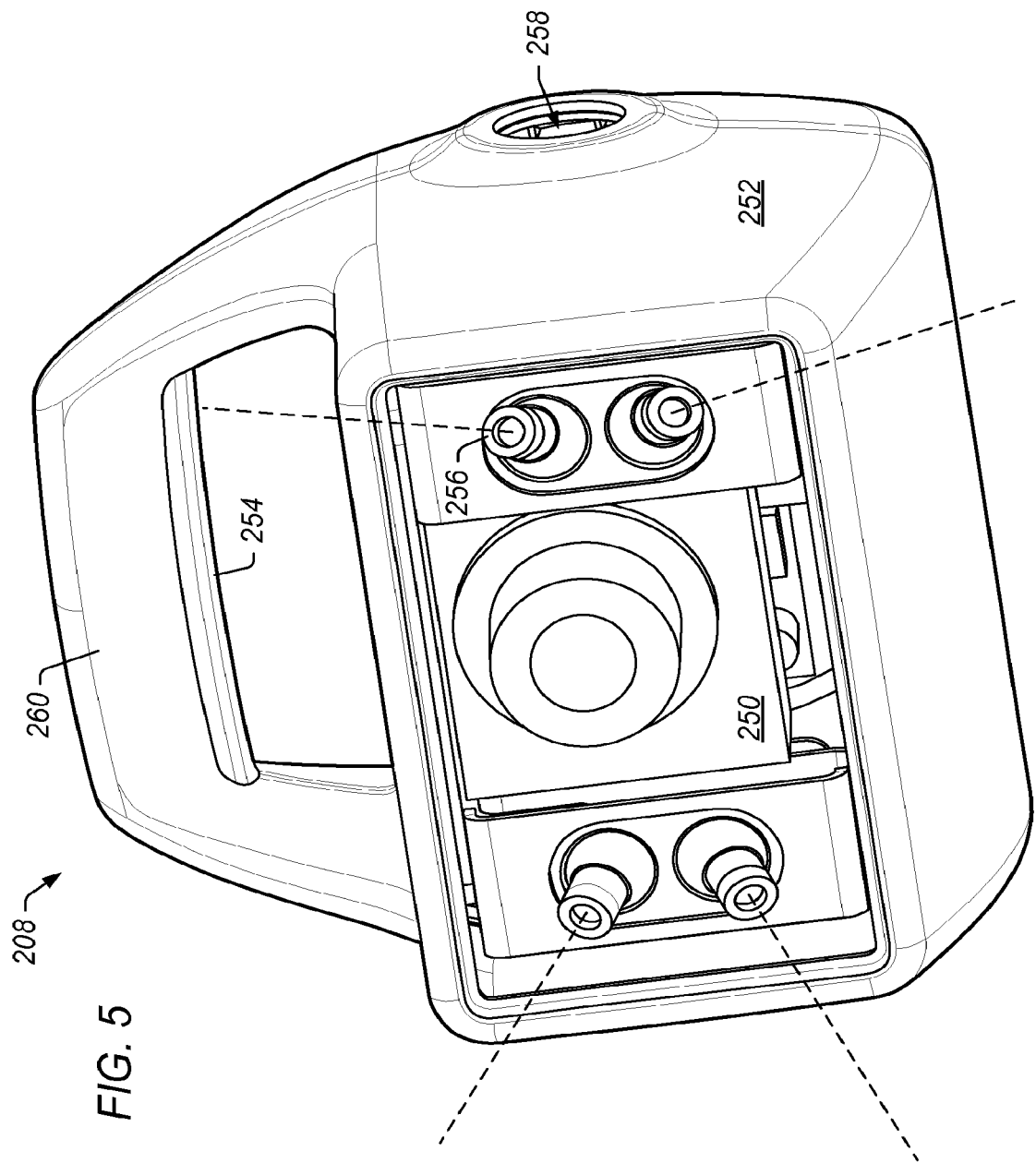
FIG. 5 illustrates one embodiment of a camera assembly for a workstation.

In some embodiments, an image capture device includes a camera for acquiring images of stages of a medication preparation. The images may be include, for example, still photographs, video clips, or live video feeds. FIG. 5 illustrates one embodiment of a camera assembly for a workstation. FIG. 5 shows a camera as viewed from generally below the camera as installed on a rail. Camera assembly 208 includes camera 250, case 252, release 254, and indicating devices 256. Case 252 may protect camera 250 from exposure to elements at a workstation, such as fumes and splashed liquids. A camera case may include, for example, gaskets and other seals. Case 252 may facilitate cleaning of a workstation. For example, in some embodiments, the camera assembly may be sterilized by wiping down the camera case with a bleach solution. In certain embodiments, a case for a camera is splash resistant.

Hole 258 passes through the camera assembly 208. Hole 258 may accommodate a rail, such as rail 206 shown in FIG. 2. Camera assembly 208 may slide along rail 206. Camera case 252 includes handle 260. Handle 260 may be grasped by a technician to move camera assembly 208 along the rail.

As noted above, camera assembly 208 includes release 254. Release 254 may be spring loaded. Camera case 208 may remain fixed on the rail until release 254 is actuated. Release 254 may be actuated, for example, by grasping handle 260 and release 254 and squeezing release 254 toward handle 260.

Indicating devices 256 may project onto the surface of a table (such as table 202 shown in FIG. 2). Each of indicating devices 256 may point at an angle relative to the direction that camera 250 is pointed. For example, with reference to FIG. 2, each of indicating devices 256 may project one of points 259 onto table 202. Points 259 may define the corners of visual reference zone 261. In one embodiment, indicating devices include dot focus lasers. For example, indicating devices may be dot focus lasers, 3.5V-4.5 V 16 mm, 5 milliwatts. Visual reference zone 261 may generally correspond to, and provide a visual reference points to a technician for, a field of view of camera 250 (which may be, for example, zone 210). A visual reference zone for a camera may, however, deviate in size, shape, and position from the field of view of a camera. For example, as shown in FIG. 2, visual reference zone 261 is smaller than zone 210.

Figure 6:
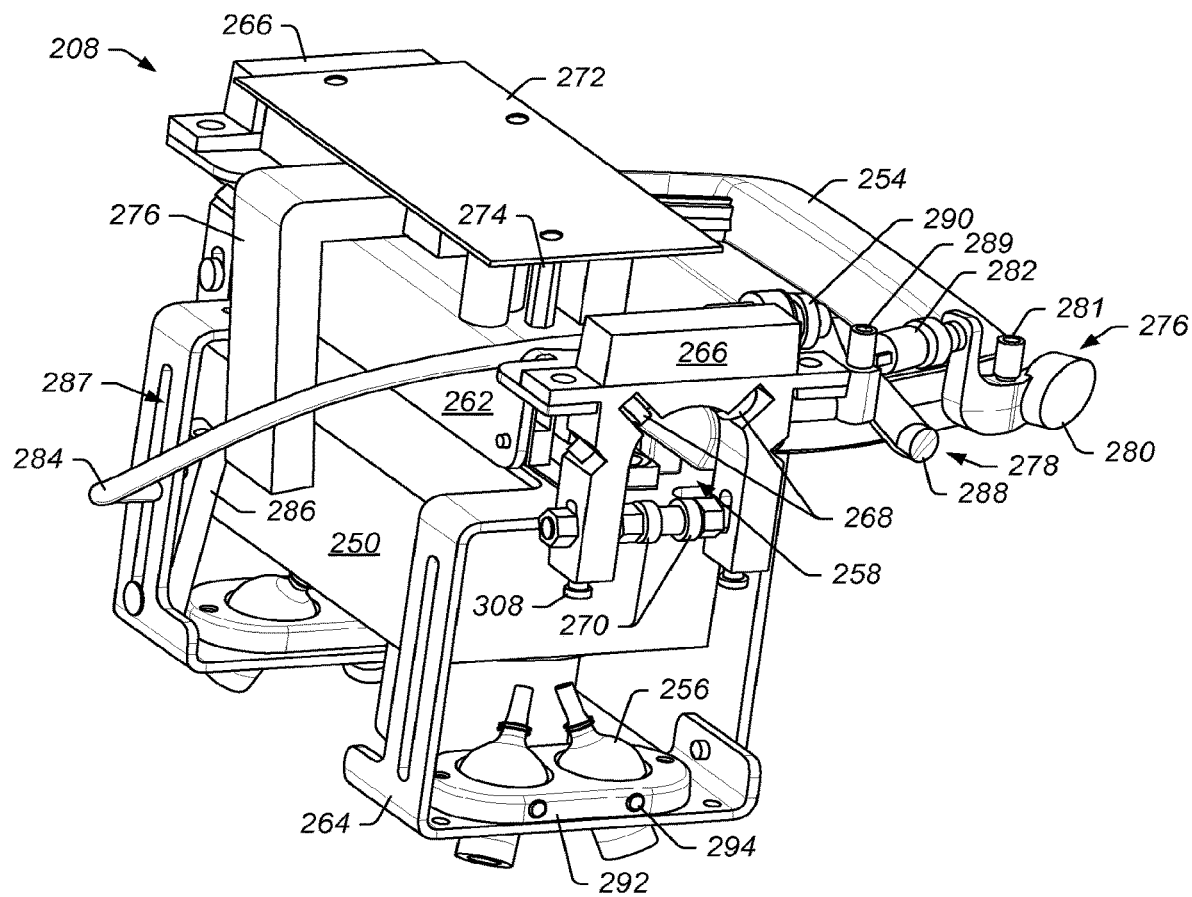
FIG. 6 illustrates an embodiment of a camera assembly in which the camera case has been removed.

FIG. 6 illustrates an embodiment of camera assembly 208 in which camera case 252 has been removed for illustrative purposes. Camera assembly 208 includes camera mount 262 and accessory bracket 264. Camera 250 is mounted to camera mount 262. Camera mount 262, in combination with bearing race assemblies 266, may serve as a carrier for camera 250. Bearing race assemblies 266 are provided at either end of camera assembly 208. Bearing race assemblies 266 are coupled to camera mount 262. Bearing race assemblies 266 include upper bearings 268 and lower bearings 270. Bearings 268 and 270 may engage a rail (such as rail 206 shown in FIG. 2) to facilitate translation of camera assembly 208 on the rail. Bearing race assemblies 266 may also be integrated into supporting features molded into the two halves of the protective case.

Circuit board 272 is mounted on camera mount 262 by way of standoffs 274. Circuit module 272 may be coupled to camera 250. Circuit module 272 includes wireless device 276. Wireless device 276 may include, in various embodiments, a USB dongle or other wireless antenna (such as wi-fi or Bluetooth). Circuit module 272 may receive image data from camera 250 and transmit the data wirelessly to a computer system, such as computer system 216 shown in FIG. 2. Circuit module may also receive control instructions from a remote computer, for example, over the internet. Circuit module 272 may also provide control signals to camera 250. In some embodiments, circuit module 272 may provide power to camera 250.

In some embodiments, an image capture device includes manual triggers. The manual triggers may control functions on the camera. For example, camera assembly 208 includes photo trigger 276 and camera on/off trigger 278. Shoot trigger 276 includes photo trigger switch 280 and tactile pushbutton switch 282. Photo trigger switch 280 may be pivotally mounted on pin 281. Manually depressing photo trigger switch 280 may operate tactile pushbutton switch 282. Tactile pushbutton switch 282 may be electrically coupled to circuit module 272 and/or camera 250.

Camera on/off trigger 278 includes on/off switch 288, pushbutton switch 290, cable trigger 284, and cable positioning clamp 286. On/off switch 288 may be pivotally mounted on pin 289. On/off switch 288 may actuate pushbutton switch 290. Pushbutton switch 290 may activate cable trigger 284. Cable trigger 284 passes through slot 287 on accessory bracket 264. Cable trigger 284 may depress a power on/off button on camera 250. Cable positioning clamp 286 is mounted on accessory bracket 264. Cable positioning clamp 286 may be adjusted to position cable trigger 284 at the proper location to depress the power on/off button. In some embodiments, cable positioning clamp 286 is adjusted to accommodate different models of cameras used for camera 250. Cable position clamp 286 may, for example, be adjusted such that cable trigger 284 is aligned with the on/off button on a particular make of camera.

Although in the embodiment shown in FIG. 6, photo trigger 276 and camera on/off trigger 278 are operated with hand-operated switches, in certain embodiments, camera control, power on/off, or both, may be carried out using foot pedals.

Accessory bracket 264 carries gimbal ring assemblies 292. Each of gimbal ring assemblies 292 carries a pair of indicating devices 256. Indicating devices 256 are mounted in an "eyeball" arrangement such that indicating devices can be adjusted to be point in various directions. In one embodiment, each of indicating devices is positioned at a desired angle to define a visual reference frame on a surface below the camera. When indicating devices 256 are in position, set screws 294 may be tightened down to lock the positions of indicating devices 256.

Figure 7:
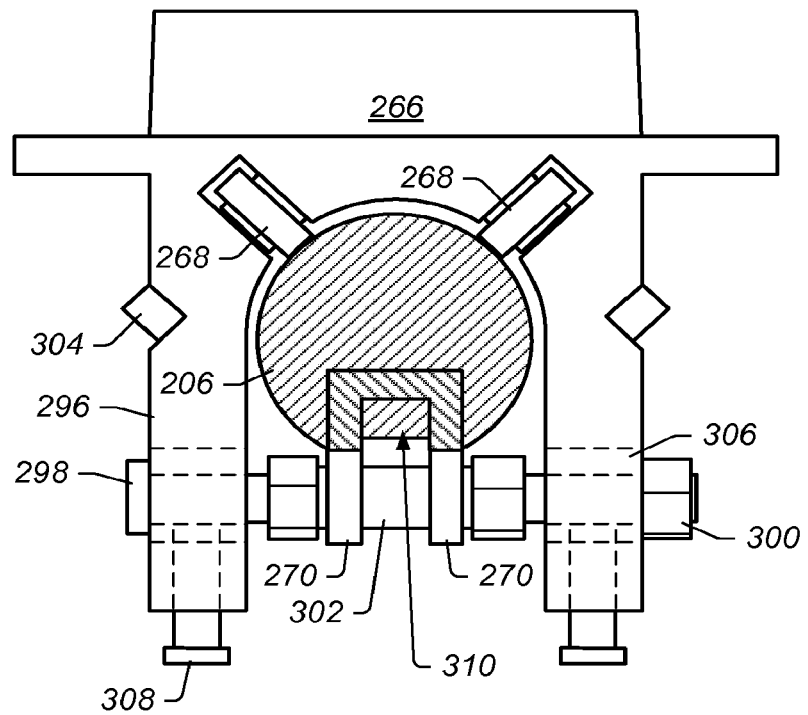
FIG. 7 is a cross sectional view of a bearing race assembly on a rail according to one embodiment.

FIG. 7 is cross sectional view of a bearing race assembly on a rail according to one embodiment. Bearing race assemblies may be provided on a camera assembly. Bearing race assembly 266 rides on rail 206. Bearing race assembly includes race 296, upper bearings 268, and lower bearings 270. Upper bearings 268 may engage the curved surface of rail 206. Lower bearings 270 may engage a flat face 310 of rail 206. Lower bearings 270 are supported on screw 298. Screw 298 may be retained by nuts 300. In some embodiments, nuts 300 are locking nuts (with, for example a nylon insert). Bushing 302 is provided between bearings 270. Upper bearings 268 are carried on set screws 304.

In some embodiments, a bearing system includes an adjustment mechanism for established desired resistance to translation along a rail. In the embodiment shown in FIG. 7, screw 298 is received in slots 306. Set screws 308 may be tightened to raise screw 298. Raising screw 298 may increase a clamping force on rail 206. In some embodiments, a clamping force is set when the camera is initially installed on a rail.

Figure 8:
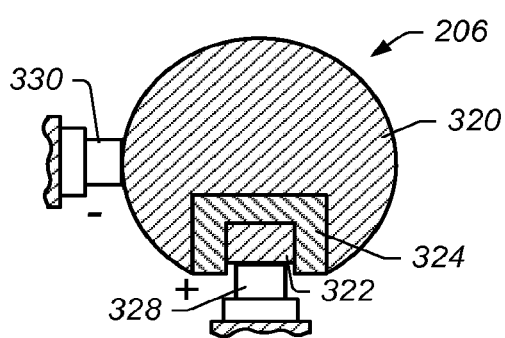
FIG. 8 illustrates one embodiment of a power connection between a rail and a camera assembly.

In some embodiments, a rail supplies electrical power to an image capture device. FIG. 8 illustrates one embodiment of a power connection between rail and a camera assembly. Rail 206 includes outer rail 320, inner rail 322, and insulator 324. Outer rail 320 and inner rail 322 may be electrically conductive. Positive contact 328 and negative contact 330 may be included on camera assembly 208. Positive contact 328 may engage on inner rail 322. Negative contact 330 may engage on outer rail 320. Positive contact 328 and negative contact 330 may slide along their respective rail as camera assembly 208 is moved along rail 206. Positive contact 328 and negative contact 330 may be coupled with, and provide electrical power to, devices in camera assembly 208, such as circuit module 272, camera 250, and indicating devices 256. In some embodiments, the power is a low voltage direct circuit ("DC") power.

In some embodiments, a rail may includes three or more conductive elements. Conductive elements on a rail may be isolated from each other with an insulating channel. In various embodiments, conductive elements of a rail may be used to transfer power, data, or provide a ground path for electronics.

Figure 8A:
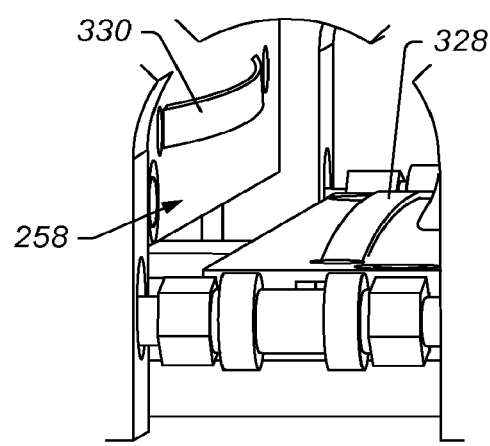
FIG. 8A is a perspective view illustrating the interior of a passage for a rail according to one embodiment.

FIG. 8A is a perspective view illustrating the interior of a passage for a rail according to one embodiment. Positive contact 328 is located along the bottom side of hole 258. Negative contact 330 is located along the rear side of hole 258. Positive contact 328 and negative contact 330 may be spring contacts. The spring contacts may resiliently engage a rail, such as rail 206.

Figure 9:
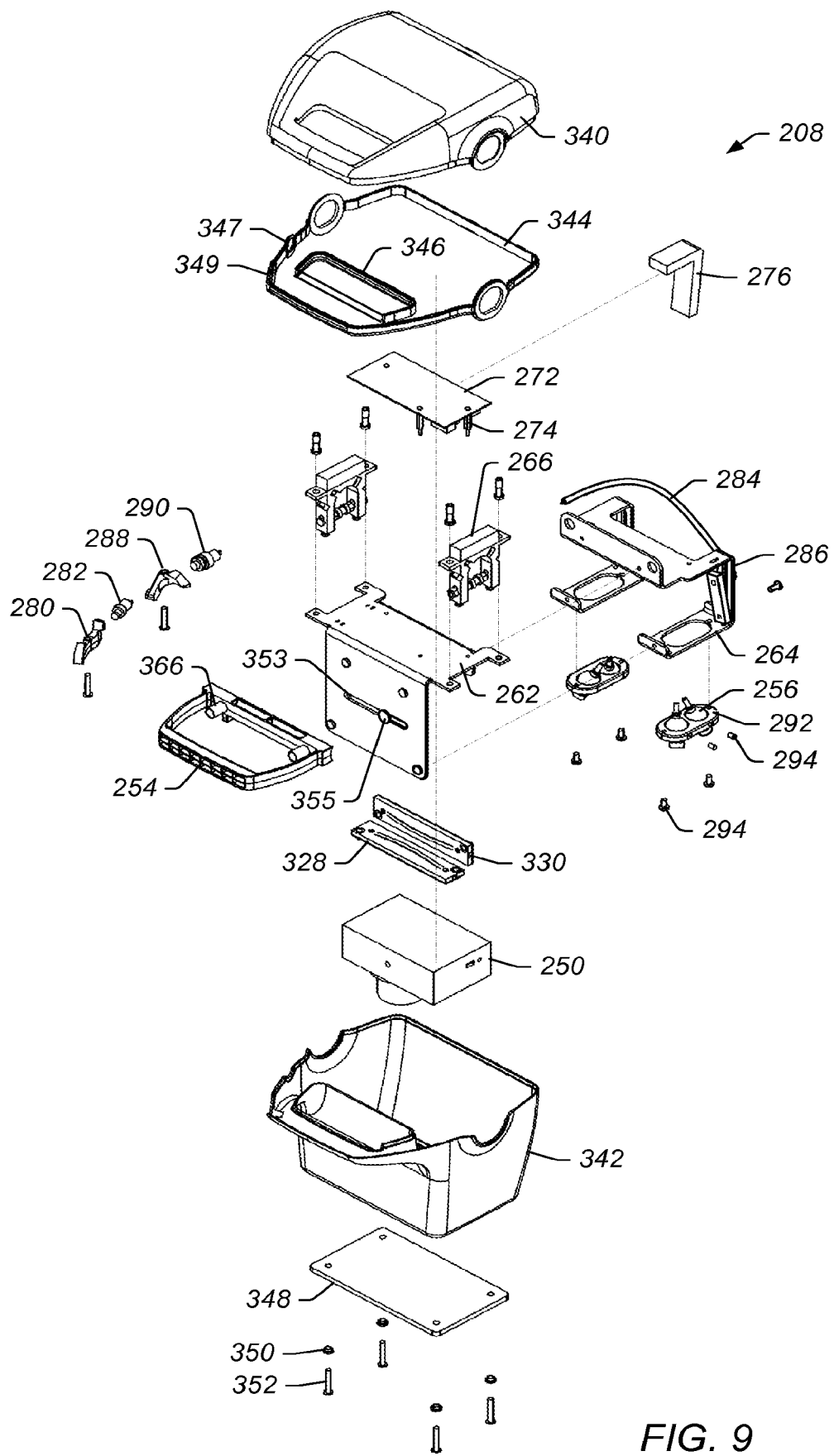
FIG. 9 is an exploded view of a camera assembly.

FIG. 9 is an exploded view of a camera assembly. Camera assembly 208 includes case top 340 and case bottom 342. Gaskets 344 and 346 are provided between case top 340 and case bottom 342. Gaskets 344 and 346 may at least partially seal the camera case, such as during a cleaning wipe-down. Gasket 344 includes pad 347 and pad 349. Pad 347 may cover on off switch 288. Pad 349 may cover photo switch 280. Pad 347 and pad 349 may inhibit fluids and/or contaminants from passing into camera assembly 208 at the apertures for the manual switches, and thereby facilitate cleaning of camera assembly 208 (such as during a wipe-down of the camera case).

Glass plate 348 is coupled to case bottom 342 with screws 352. Grommets 350 may seal the camera case at the mounting location of glass plate 348.

Camera mount 262 includes slot 353. Screw 355 may pass through slot 353. Screw 355 may engage in a threaded socket in camera 250 (such as a threaded socket for a standard tripod mount). Screw 355 may be adjustable in slot 353. Adjustment of screw 355 may be used to accommodate different models of cameras as camera 250.

Release 254 includes arcuate face 364. In some embodiments, arcuate face 364 of release 254 bears against the side of rail 206 (for example, under the force of springs 366). When release 254 is engaged against the rail, rotation of camera assembly 208 with respect to rail 206 may be inhibited or prevented. In addition, when release 254 is engaged against the rail, translation of camera assembly 208 along rail 206 may be prevent or inhibited. Release 254 may be operated by a user to disengage release 254 from rail 206.

Figure 10:
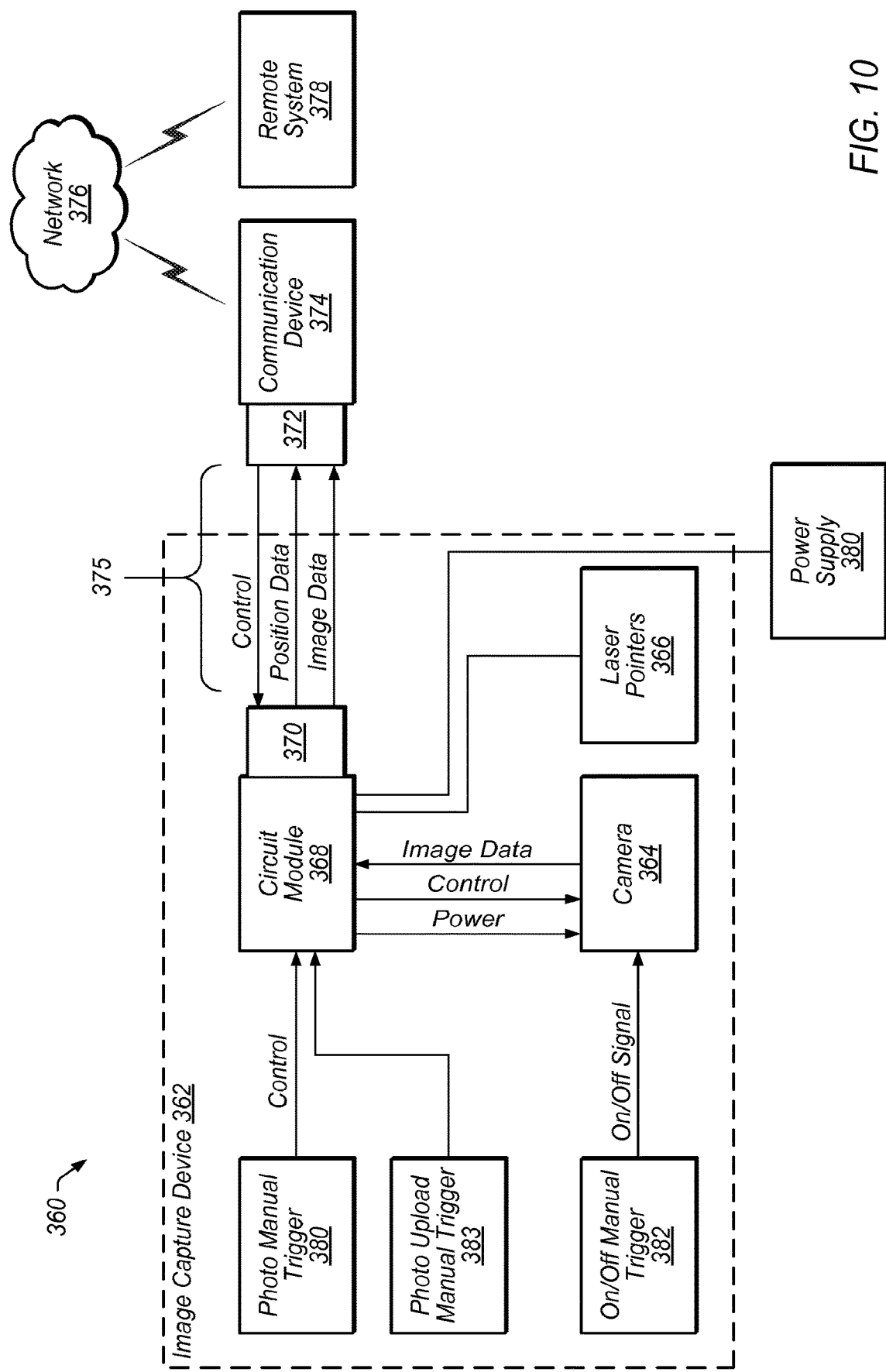
FIG. 10 is a schematic diagram illustrating one embodiment of a system including an image capture device with a wireless transmitter/receiver.

In some embodiments, an image capture device communicates with a computer system through a wireless connection. FIG. 10 is a schematic diagram illustrating one embodiment of a system including an image capture device with wireless transmitter/receiver. System 360 includes image capture device 362. Image capture device 362 may include, for example, camera assembly 208 described above relative to FIGS. 2-9. Image capture device 362 includes camera 364, laser pointer 366, and circuit module 368. Circuit module 368 may provide and control power to camera 364 and laser pointer 366. In certain embodiments, power from a circuit module to a camera may be varied or adjusted. In one embodiment, power is varied to accommodate a different model camera for camera 250.

Circuit module 368 includes wireless transmitter/receiver 370. Wireless transmitter/receiver 370 may transmit and receive information to and from a corresponding transmitter/receiver 372 on communication device 374 over wireless connection 375. Communication device 374 may be, for example, a personal computer system near a workstation where image capture device 362 is being used, or a wireless network hub. Wireless connection 375 may be used to transfer control signals or position data (such as whether a manual trigger has been actuated on image capture device 362). Wireless connection 375 may also be used to transfer image data from camera 364 to communication device 374, which may, in turn, send the image data to remote computer systems such as remote computer system 378.

Communication device 374 may be connected via network 376 to remote computer system 378. Remote computer system 378 may be, for example, a computer system used by a pharmacist to supervise preparations being photographed with image capture device 362. Remote computer system 378 may also be used to control the camera directly through the network or communication device 374.

Circuit module 368 may receive power from power supply 380. In some embodiments, power may be transmitted to circuit module by way of conductors in a rail on which the image capture device is mounted, such as rail 206 described above relative to FIGS. 2-9. Circuit module 368 may distribute power to camera 364 and laser pointers 366.

In some embodiments, shooting of an image by a camera may be triggered by a user either from a computer system input/output device (such as a mouse of computer system 374) or by a user-operated switch. A user-operated switch may be located, for example, on the case of an image capture device, on a foot pedal switch, or in any other location. In some embodiments, the switch is located outside of a clean zone in which preparations are made. For example, a user operated trigger may be located in a foot pedal on the floor of a room outside of a hood in which preparations are made. In some embodiments, a switch is a remote switch (for example, operated from a device or computer system in a different room.

Image capture device 362 includes manual trigger photo switch 380, manual trigger on/off switch 382, and photo upload manual trigger 383. Manual trigger photo switch 380, manual trigger on/off switch 382, and photo upload manual trigger 383 may be located on a camera case of image capture device 362. Manual trigger photo switch 380 may signal circuit module 368 to trigger shooting of a photo with camera 364. Alternately, computer system 374 may send a signal to circuit module 368 to trigger shooting of a photo. In some embodiments, the control signal from manual trigger photo switch 380 is passed by circuit module 368 to computer system 372 over wireless connection 375. Upon receipt of the signal, computer system 372 may return a control signal to circuit module 368 over wireless connection 375 for the camera to take the photograph. Photo upload manual trigger 383 may be operable by a user to upload images that have been acquired using image capture device 362.

Manual trigger on/off switch 382 may be operated by a user to switch power on and off in camera 364. In one embodiment, circuit module 366 and/or computer system 374 may monitor whether camera 364 is powered up. If camera 364 is powered up, circuit module 366 may activate or maintain power to laser pointers 366. If camera 364 is not powered up, circuit module 366 may place or maintain laser pointers 366 in a powered-off state. Although in the embodiment shown in FIG. 10, manual trigger on/off switch 382 is directly connected to the camera, a manual power on/off switch for a camera may in some embodiments operate by sending an electronic signal to a circuit module. Switch 382 may alternatively be an upload switch (for example, allowing the technician to send the image to a pharmacist at a remote workstation.)

Figure 11:
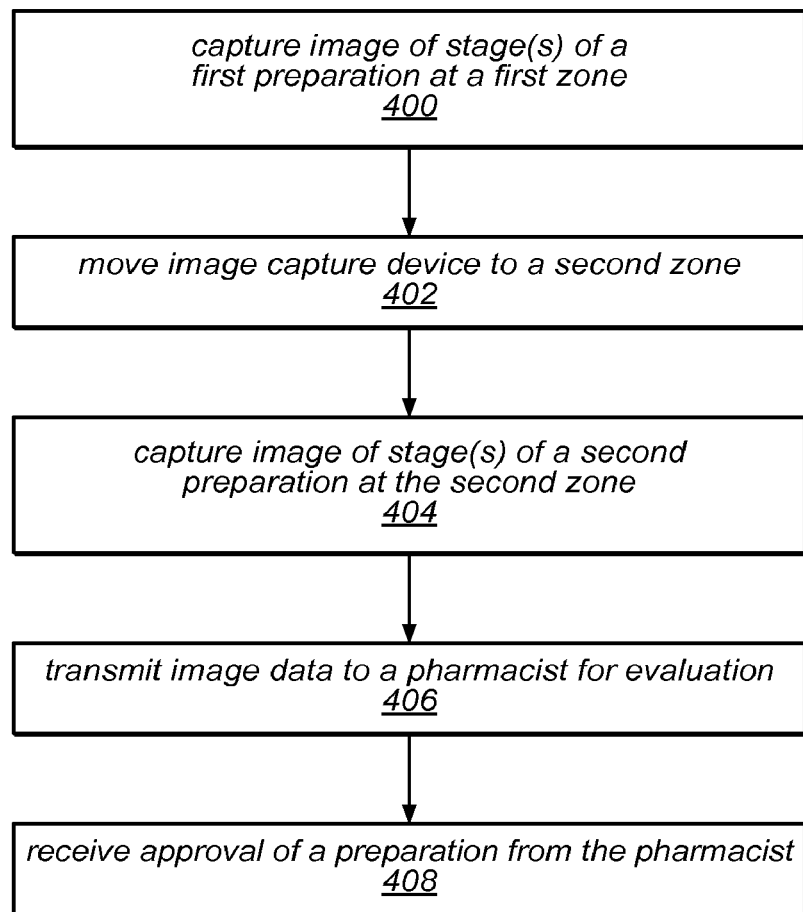
FIG. 11 illustrates sequentially capturing image data for two or more preparations according to one embodiment.

In some embodiments, an image capture device may be positioned to sequentially capture images of preparations occurring at two or more different locations at a workstation. In one embodiment, the image capture device is positioned by translating the image capture device from one position to another. For example, the image capture device may be slid on an overhead rail, such as rail 206 described above relative to FIGS. 2-9. FIG. 11 illustrates sequentially capturing image data of for two or more preparations according to one embodiment. At 400, an image of a stage in one preparation is captured at a first zone at a workstation using an image capture device. At 402, an image capture device is moved (for example, translated) such that the image capture device points at a second zone. At 404, an image is captured of a stage of preparation for a second preparation that is being prepared at the second zone. At 406, the image data is transmitted to a pharmacist for evaluation. At 408, the pharmacist may approve a preparation (or a step in the preparation) based on the review of the image.

In some embodiments, multiple images may be uploaded to a website or bulletin board as a single post and inclusion of multiple images in a single post may indicate all of the included images are part of a single pharmacy task that requires remote supervision and verification. Alternatively, in other embodiments, each of the captured images for a single pharmacy work task, whether for a medication order or other pharmacy work, may contain some indication that they are part of the same pharmacy work task. For example, in one embodiment, each related image could include a unique reference number associated with the pharmacy work task. Reference numbers may be included in captured images using a number of different techniques, according to various embodiments. For example, in one embodiment, a small piece of paper with a reference number printed on it may be in the view of an image capture device when each image is captured. In another embodiment, reference numbers may be overlayed on, inserted in, or otherwise graphically added to the captured images. In yet other embodiments, an image capture device may be configured to automatically graphically include, add, or overly reference numbers to captured images. An order identification number from a medication order may be included as a reference number in captured images, according to one embodiment. In other embodiments, reference numbers may be generated for each set of related images, such as by an order entry system for entering medication information into a patient's medication profile. In general, any type or sort of reference indicators, either alphanumeric or graphical, may be used to indicate related captured images.

In some embodiments, an image capture device captures an image of a stage in a medical preparation. The image may include an identifier code associated with the preparation. The identifier code may be, for example, a semacode or bar code that corresponds to a particular medication, procedure, or task. In one embodiment, the identifier code is positioned so that it appears in the same position in all of the acquired images (such as in the lower left corner of the image).

In some embodiments, two or more medications are prepared at different workstations, or at different areas of the same workstation. For each preparation, an appropriate identifier code may be included in the images associated with the preparation. The various images required for the preparations may be captured in any sequence. The identifier information may be read from captured images. A computer system may associate, reorder, group, or otherwise manage the various images based on the identifier code information.

In some embodiments, workflow to a pharmacist may be batched. For example, one or more preparations at a workstation (or at different workstations) may be batched in a first priority batch, and one or more other preparations at the workstation (or at different workstations or locations) may be placed in second, lower priority batch, and so on. A pharmacist might evaluate the first priority preparations first, and then evaluate the lower priority batches in turn. In any of these examples, the various priority preparations may be prepared at any given time, and in any sequence (for example, at different workstations, or using the movable image capture device described herein). In some embodiments, workflow of the preparations or evaluations may be interrupted. For example, a pharmacist might stop evaluations for a break, or be relieved by a pharmacist on a succeeding shift.

FIGS. 12A-12G is a schematic diagram illustrating one embodiment of acquiring images for multiple preparations at a workstation. Workstation 410 includes substations 412A, 412B, and 412C. Image capture device 411 is mounted on rail 413. Image capture device 411 may be translated along rail 413 to sequentially acquire images at workstations 412A, 412B, and 412C. When image capture device is at station 412A, image capture device may capture an image that includes zone 414A. When image capture device is at station 412B, image capture device may capture an image that includes zone 414B. When image capture device is at station 412C, image capture device may capture an image that includes zone 414C.

Figure 12A:
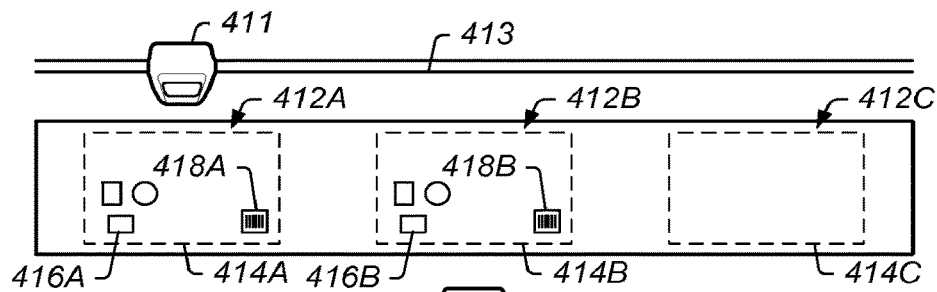
FIGS. 12A-12G is a schematic diagram illustrating one embodiment of acquiring images for multiple preparations at a workstation.

In FIG. 12A, preparations are commenced at substation 412A and substation 412B. Image capture device 411 may capture an image at a first stage of preparation at substation 412A. The image at the first stage may include constituents 416A and identifier code 418A.

Figure 12B:
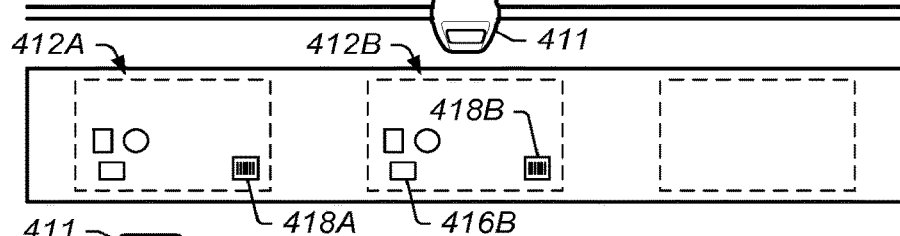

In FIG. 12B, image capture device is moved from substation 412A to substation 412B. Image capture device 411 may capture an image at a first stage of preparation at substation 412B. The image at the second stage may include constituents 416B and identifier code 418B.

Figure 12C:
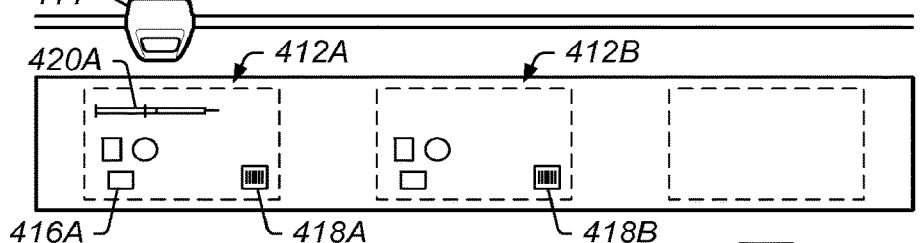

In FIG. 12C, image capture device is moved from substation 412B back to substation 412A. Image capture device 411 may capture an image at a second stage of preparation at substation 412A. The image at the second stage may include constituents 416A, syringe 420A, and identifier code 418A. Syringe 420B may be pulled back to show, for example, a quantity of saline solution to be used in the preparation. Identifier code 418A is the same identifier code that was present in the image when an image was captured at the first stage of preparation at substation 412A.

Figure 12D:
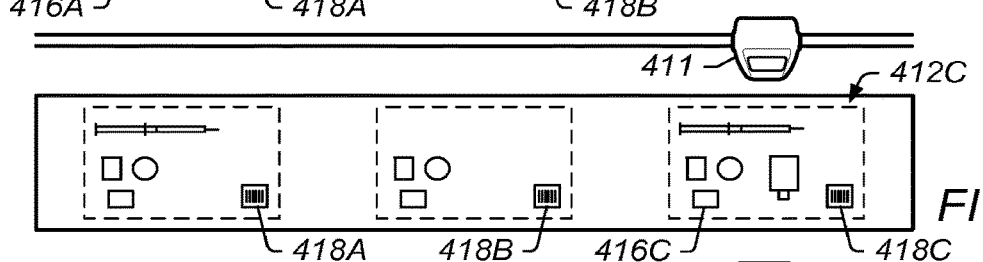

In FIG. 12D, a high priority order may be received. The high priority order may be, for example, a chemotherapy medication that is urgently needed for a particular patient. A second technician may immediately commence preparation at substation 412C. Image capture device may be moved to substation 412C and an image captured of constituents 416C and identifier code 418C. In this example, identifier code 418C may include a "STAT" code.

Figure 12E:
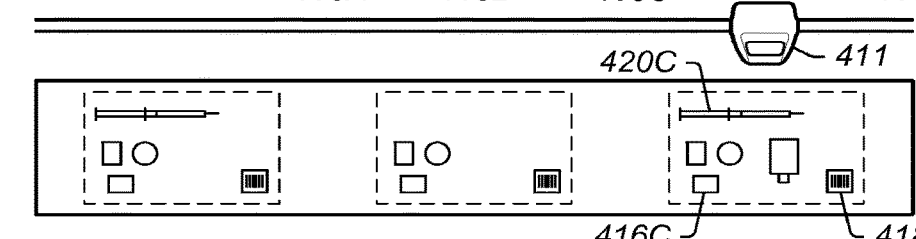

In FIG. 12E, preparation of the high priority preparation is continued at substation 412C. Camera 411 may remain in position at substation 412C. In some embodiments, image data is transferred to a pharmacist at each stage as soon as the image is taken. The pharmacist may review and approve the stage before the next stage is commenced. An image may be acquired of a second stage of preparation at 412C that includes constituents 416C, syringe 420C, and identifier code 418C.

Figure 12F:
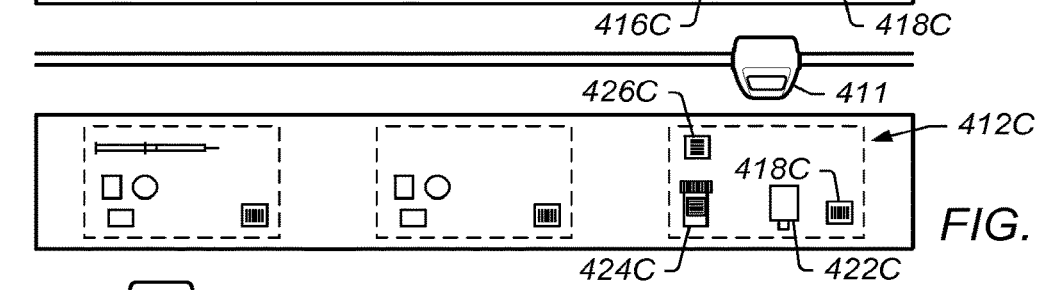

In FIG. 12F, preparation of the high priority preparation is continued at substation 412C. Camera 411 may remain in position at substation 412C. An image may be acquired of a third stage of preparation at 412C that includes medicine 422C, vial 424C, label 426C, and identifier code 418C.

Figure 12G:
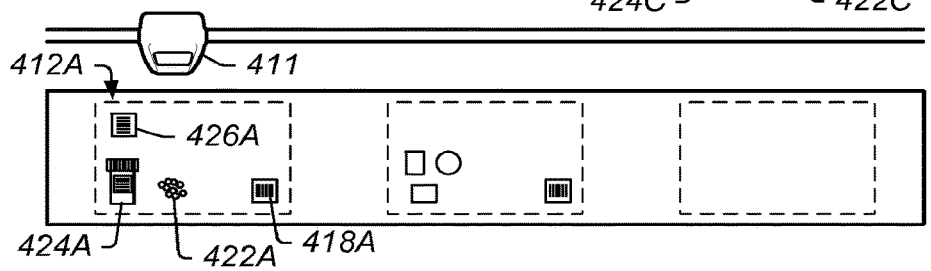

In FIG. 12G, preparation of the lower priority preparations may be re-commenced at substation 412A. Camera 411 may be moved to substation 412A. An image may be acquired of a third stage of preparation at 412A that includes medicine 422A, vial 424A, label 426A, and identifier code 418A. The preparation started at substation 412B may then be completed.

In various embodiments, identifier information, such as identifier codes 418A, 418B, and 418C, may be automatically read from preparation images. The identifier information read from the images may be used so that the images for particular preparations can be associated, grouped, ordered or reordered automatically by a computer system. In the embodiment described relative to FIGS. 12A-12G, for example, the pharmacist may review the images taken at substation 412A for all three stages of a preparation as one group, the images for all three stages of a preparation taken at substation 412B as another group, and the images taken at substation 412C as a third group. The pharmacist may have the option of prioritizing the preparations. For example, the pharmacist may review and approve the high priority preparation tasks carried out at substation 412C before reviewing the lower priority preparation tasks carried out at substations 412A and 412B.

In some embodiments, a foot pedal system is used to capture and use images of a preparation and associated documentation. One or more different functions may be assigned to each pedal. For example, a technician may use a foot pedal to select an existing job and to add images to the job. In one embodiment, a foot pedal assembly includes three pedals. The user may repeatedly click on the first pedal to sequentially highlight preparation jobs on a list on a computer monitor. The user selects the desired job with the first pedal (for example, by holding the first pedal for a specified duration, such as 3 seconds). When the job is selected, information about the job may come up on the monitor. The first image in the job may be, for example, a computer-generated medication preparation instruction sheet (compounding sheet). Once the job is displayed on the monitor, the user may press a second pedal to add an image to the job. The third pedal may be operated to send the job to a pharmacist for review.

In some embodiments, a foot pedal may be used to initiate new jobs. For example, from the job list page in the example described above, the user may press the second pedal to initiate a new job and capture an image for the new job. The user can use the second pedal to add images to the new job and the third pedal to send the job to the pharmacist as described above.

In some embodiments, a foot pedal system is used in a manner such that a preparation is completed without the need for paper documents to be brought into the sterile environment.

Figure 12Y:
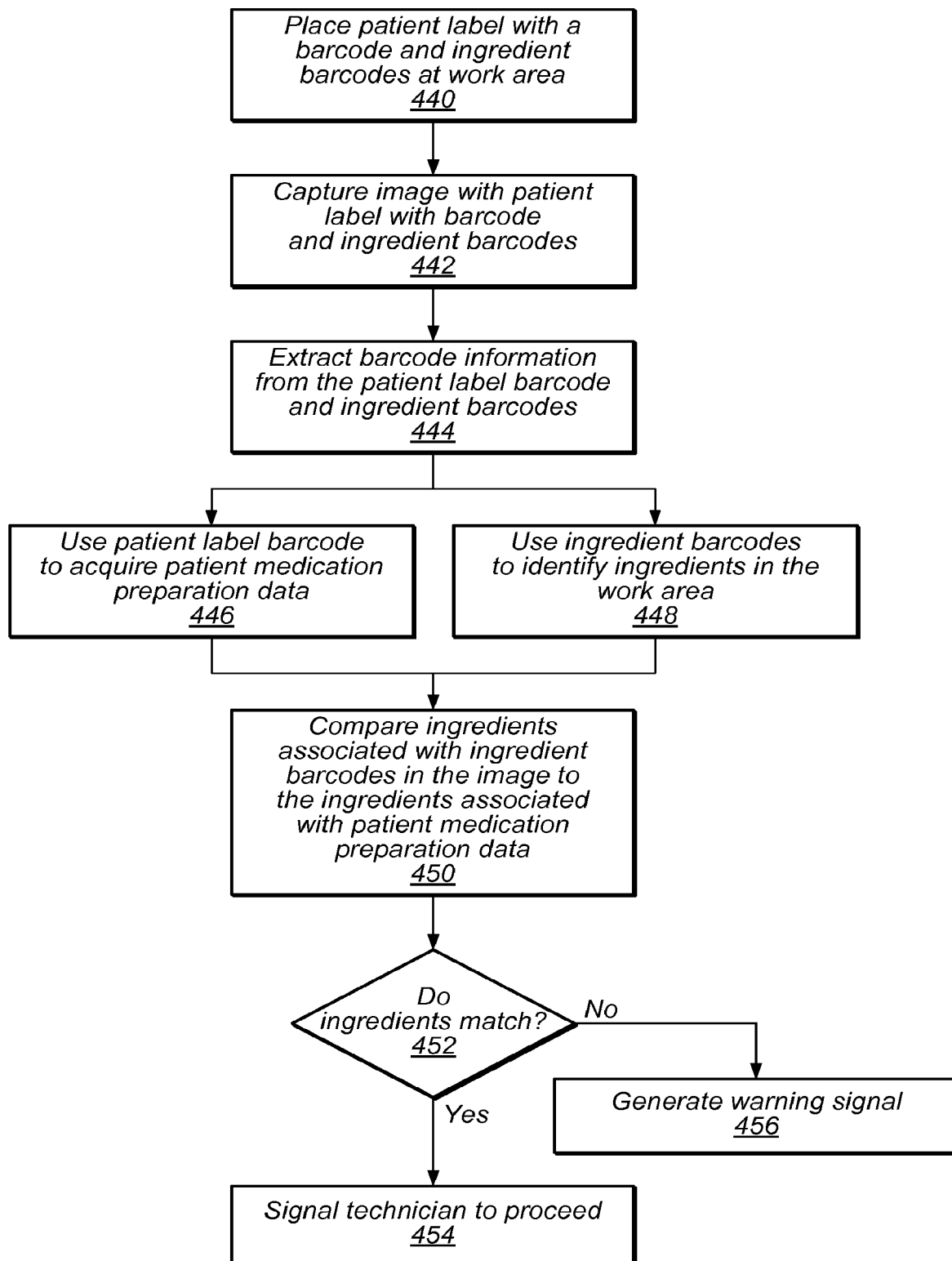
FIG. 12Y illustrates one embodiment of verifying ingredients of a patient preparation by comparing barcodes in an image.

In some embodiments, identifier codes in images are used to automatically check ingredients at a workstation against patient preparation data. In some embodiments, a computer system uses barcode recognition to compare an ingredient identifier in an image with another identifier in the image that is associated with a patient, or associated with a patient preparation. FIG. 12Y illustrates one embodiment of verifying ingredients of a patient preparation by comparing barcodes in an image. At 440, a patient label with a barcode and one or more ingredient barcodes are placed at a workstation. For example, in the arrangement shown in FIG. 2A, documentation 228 may include a patient preparation label with a barcode and documentation 230 may include an ingredient label with a barcode.

Referring again to FIG. 12Y, at 442, an image is captured that includes the patient label with the barcode and one or more of the ingredient barcodes. At 444, a computer system (such as a server) extracts barcode information from the patient label barcode and one or more of the ingredient barcodes. At 446, the computer system uses the patient label barcode number to acquire patient medication preparation data from, for example, an order entry system. The patient medication preparation data may include the ingredients that should be included in the preparation. At 448, the computer system may use ingredient barcodes (for example, a National Drug Code ("NDC")) or a drug barcode database to identify the ingredients that are actually at the preparation surface. At 450, the computer system may compare ingredients in the image with the ingredients acquired from the patient medication preparation data. At 452, a determination is made of whether the ingredients actually at the preparation surface match the ingredients specified in the medical preparation data. If the ingredients match, a signal may be given to the technician to proceed at 454. If the ingredients do not match, a warning signal may be generated by the system and sent to the technician, a remote pharmacist, or other persons at 456.

Figure 13:
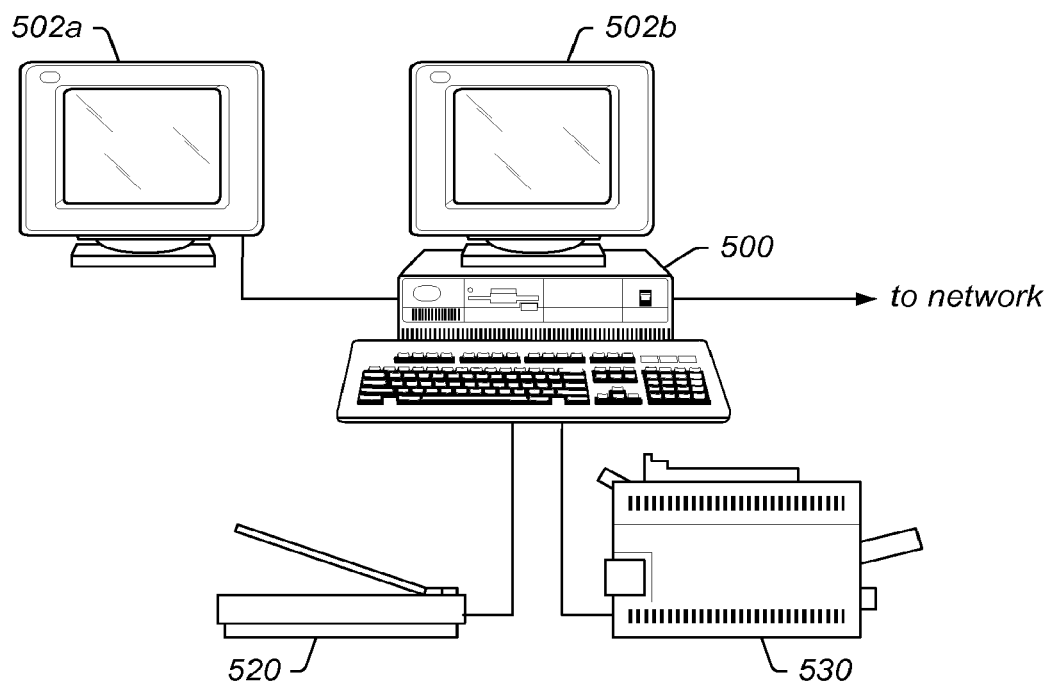
FIG. 13 illustrates one embodiment of an exemplary remote pharmacist workstation.

Remote Pharmacist Site:

FIG. 13 illustrates an exemplary workstation used by a pharmacist at remote pharmacist site 110, according to some embodiments. A remote pharmacist workstation may include a computer 500 with one or more monitors, such as monitors 510a and 510b, allowing viewing captured images of pharmacy work performed as preparation site 120. According to some embodiments, a remote pharmacist workstation may include two monitors 510 coupled to computer 500 to allow simultaneous viewing of two images. A remote pharmacist workstation 110 may also have Internet connectivity for communicating with preparation site 120, according to one embodiment. A remote pharmacist workstation 110 may, in some embodiments, also include, but is not limited to, a scanner 520, a printer 530, telephone, fax machine, and/or a copier. A remote pharmacist workstation may communicate with one or more preparation sites 120 and/or with system website 130 via an Internet connection, virtual private network, LAN, WAN, or in general any wired or wireless link, according to various embodiments.

In some embodiments, more than one pharmacist may be on duty at a single remote pharmacist site 110 and thus a remote pharmacist site 110 may include more than one remote pharmacist workstation. In such an embodiment, multiple remote pharmacist workstations may be linked via a local network, such as a LAN or WAN, and each workstation may be configured to communicate via an Internet connection provided by the local network.

Each remote pharmacist site 110 may have one or more pharmacist on duty, as well as other non-pharmacist support personnel, according to various embodiments. Any pharmacist that remotely supervises and/or verifies pharmacy functions performed by non-pharmacist personnel at preparation site 120 from a remote pharmacist site 110 may be required to have licensure to practice pharmacy in the state in which the preparation site 120 being serviced is located, in accordance with state laws. As noted above, a pharmacy function performed at preparation site 120 may be remotely supervised and verified by a pharmacist at a pharmacist site remotely located from preparation sites 120, according to various embodiments. In general a remote pharmacist site 110 may be in any location, including different pharmacy from a pharmacy at the preparation site. In certain embodiments, a pharmacist located in one part of an institution may remotely supervise and verify pharmacy functions performed in multiple preparation sites 120 (e.g., institutional pharmacies or teaching institutions) located in other parts of the same institution. For example, a large institution may include one or more different pharmacy stock areas, or satellite pharmacies, that operate under a single pharmacy license and in some embodiments pharmacy functions performed at satellite pharmacies may be remotely supervised and verified by a remote pharmacist either on duty in a main pharmacy, a different one of the satellite pharmacies, or located offsite. Alternatively, in other embodiments, an institution may include more than one pharmacy and pharmacy functions performed at one pharmacy may be remotely supervised and verified by a pharmacist at a different one of the pharmacies.

A remote pharmacist site 110 may even change physical locations over time, according to some embodiments. For example, in one embodiment, a pharmacist working at a remote pharmacist site 110 in Texas may service preparation sites 120 in Utah. Such a pharmacist may leave Texas and travel to another location, perhaps Colorado, and may continue to service the preparation sites in Utah. For instance, the pharmacist may leave Texas after a shift of work there, and may arrive in Colorado before her next scheduled shift with the preparation sites in Utah. Given the portable nature of modern computer equipment, a pharmacist may take a remote pharmacist workstation, such as illustrated in FIG. 13, while traveling between remote pharmacist sites 110, according to one embodiment.

According to some embodiments, a single remote pharmacist site 110 may service more than one preparation site 120 and a single preparation site 120 may be served by more than one remote pharmacist site 110. Additionally, more than one pharmacist may work at a remote pharmacist site 110. In general, any pharmacist at any remote pharmacist site 110 may remotely supervise and verify pharmacy work performed at any preparation site 120, according to some embodiments. For example, preparation site 120 may be serviced by one pharmacist at remote pharmacist site 110a on Mondays and may be serviced by a different pharmacist, either at the same remote pharmacist site or a different remote pharmacist site, on Tuesdays. On Wednesdays, preparation site 120 may be serviced by a pharmacist at remote pharmacist site 110b. Additionally, according to one embodiment, preparation site 120 may be serviced by two (or more) different remote pharmacist sites at the same time while a single pharmacist at a remote pharmacist site may service two different preparation sites at the same time.

According to some embodiments, multiple captured images for a single pharmacy work task may be included in a single upload or post to a website or bulletin board, such as to system website 130. Including multiple images in single upload or post may, in certain embodiments, indicate that the images are all related to the same pharmacy work task. Alternatively, in another embodiment, each image may include a reference indicator that links the materials and documentation displayed to a corresponding pharmacy work task, such as a medication order. Such a reference indicator may be an original order, a copy of an original order, or a listing containing a unique medication order number generated from the patient's medication profile, such as a complete label, medication fill list, or a Medication Administration Record, according to various embodiments. The exact nature of such a reference indicator may vary from embodiment to embodiment or within a single embodiment. Additionally, any documentation required by policy or law for the pharmacy work performed may also be included in captured images used for remote supervision and verification. Such documentation may include, but is not limited to, the patient's name, the pharmacy location, the date and time, and/or the full signature and/or title of person performing the pharmacy functions or removing the medication from the pharmacy, according to different embodiments.

In some embodiments, a pharmacist may remotely verify pharmacy work via a real-time collaboration tool. For instance, software may be installed at both an institutional pharmacy site and at a remote pharmacist site allowing a pharmacist to view in real-time, or near real-time, images of the pharmacy work being performed. In one embodiment, a real-time collaboration tool may include software that interfaces with imaging device 210 to allow a non-pharmacist performing pharmacy work at an institutional pharmacy to transmit live images of the pharmacy work being performed. For example, the institutional pharmacy site and the remote pharmacist site may be connected over the Internet via a custom protocol for viewing remote pharmacy work, such as may be implemented by remote verification software 140 illustrated in FIG. 1. Alternatively, in another embodiment, a live feed from a camera capturing pharmacy work being performed may be transmitted to a remote pharmacist using standard, off-the-shelf, video conferencing and/or collaboration software. Thus, in some embodiments, a remote pharmacist may supervise pharmacy work as it is being performed. For example, in one embodiment, a remote pharmacist may verify each step as it is performed and may provide an indication to a non-pharmacist performing the pharmacy work that the step was performed correctly. In such an example, the remote pharmacist may provide verification feedback via the same collaboration software, or via another method, such as by telephone.

Figure 14:
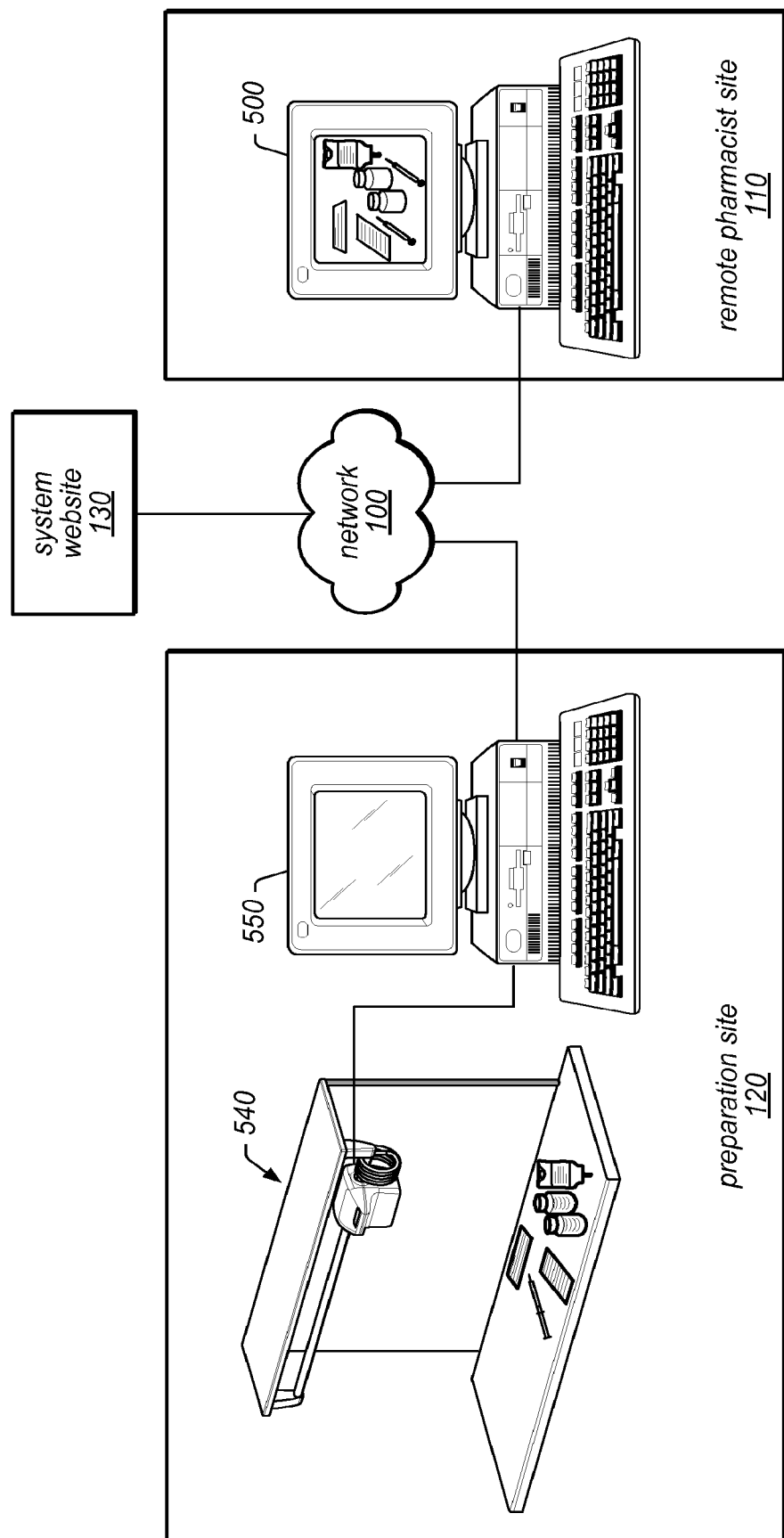
FIG. 14 illustrates an exemplary system for remotely supervising and verifying pharmacy functions, according to one embodiment.

FIG. 14 illustrates an image captured on image capture device 540 at preparation site 120 being sent and viewed at remote pharmacist site 110, in one embodiment. For example, a nurse, or other non-pharmacy personnel, at institutional pharmacy Site 120 may enter the pharmacy and compound a sterile intravenous product that was ordered for a patient after pharmacy hours and was not available outside of the pharmacy department. A pharmacist may have entered the mediation order into the patient's medication profile and may also have generated a label for the intravenous product via the pharmacy's order entry software. According to one embodiment, after visually inspecting the final product, such as for particulate matter, the nurse may place the labeled sterile intravenous product, with label and base solution content clearly visible, on image capture device 540's display area. Additionally, in one embodiment, one or more of the following items may also be placed on a display area of image capture device 540:

1. A vial of sterile water, with label (such as a barcode label) clearly visible, which was used to reconstitute the medication vial added to the final product.
2. A syringe with the plunger pulled back to the marking on the syringe that indicates the volume of sterile water used to reconstitute the medication vial.
3. The vial of medication that was reconstituted, with label (such as a barcode label) clearly visible, a portion of which was added to the final product's base solution.
4. A syringe with the plunger pulled back to the marking on the syringe that indicates the volume of reconstituted medication that was added to the base solution to prepare the final product.

If all the items listed above do not reasonably fit on the display area, the nurse may, in some embodiments, capture additional images that contain any items necessary to check the work performed. Additional items not listed above may also be included in captured images, such as a document with the current date and/or time, her full signature, and title, according to one embodiment.

The captured image(s) may be transmitted to system website 130 via a network or telecommunication link, according to one embodiment. Image capture device 540 may be coupled to computer 550 which itself may be coupled to network 100. In one embodiment network 100 may represent a local area network providing a connection to the Internet, while in other embodiments, network 100 may represent the Internet to which computer 200 may connect directly. The non-pharmacist worker may log onto system website 130 to upload the captured image(s), in one embodiment. The captured image(s) may be transmitted from the workstation at preparation site 120 to system website 130 and may be downloaded by a workstation at remote pharmacist site 110, according to some embodiments. In other embodiments, however, captured images may be directly transmitted to remote pharmacist site 110, via email for example. A pharmacist at remote pharmacist site 110 may view the pharmacy work performed at preparation site 120, as well as any other information necessary to conduct process checks and verify that the medication in the captured image(s) was correctly and accurately prepared, labeled, compounded, and/or packaged. Examples of information that may be included in captured images to allow supervision and verification of pharmacy work and medication removal may include, but are not limited to the following:

1. Medication labels, solution labels, final product labels.
2. Supplies used in compounding the product.
3. Equipment indicating volumes used in product preparation.
4. Indications of the order in which medications were added during product preparation.
5. Prescriber's order including patient name, drug name, dose, route of administration, schedule of drug administration, reason for administration, and signature of the prescriber or his agent.
6. Documentation that includes drug name, strength, lot number, expiration date, date, time, number of units to be removed from the pharmacy, worker initials, worker signature and title.
7. Auxiliary labels.
8. Special storage requirements for medication.
9. Drug information references.
10. Barcodes.

The above list is only exemplary and that the actual items and/or the number of items included in captured images may vary from embodiment to embodiment. The pharmacist may review the captured image(s) on computer 500 to verify that the nurse recorded proper documentation for record keeping purposes, according to one embodiment.

When remotely supervising and/or verifying pharmacy work performed at preparation site 120, a pharmacist at remote pharmacist site 110 may download one or more captured images from system website 130. Alternatively, captured images may be directly transmitted from preparation site 120 to remote pharmacist site 110, as described above. The pharmacist may review the medication order entry shown on the image of the patient's Medication Administration Record in one of the captured images. He may also compare it to an image showing the actual pharmacy work performed, and may verify that an order number on the Medication Administration Record matches an order number listed on the sterile intravenous product label also shown in the captured image. The pharmacist may further inspect the captured image(s) to observe one or more of the following:

1. The label on the intravenous product is complete and correct according to the medication order, properly lists the base solution used, and has been initialed by the nurse.
2. The nurse added the correct diluent and the correct and accurate volume to reconstitute the medication vial.
3. The correct medication vial was selected for reconstitution, and that the correct and accurate volume of the reconstituted medication solution was added to the final product.
4. The intravenous product has a sterile seal on the port designed for addition of medication.
5. There is no obvious particulate matter in the solution, as seen in the image.

Please note that the above list is exemplary and that the actual steps taken by a pharmacist when remotely supervising and/or verify pharmacy functions may vary from embodiment to embodiment.

The pharmacist may also indicate that the work has been supervised and/or verified according to the captured images, and is authorized for removal from the pharmacy or to be placed into regular pharmacy stock, according to one embodiment. A pharmacist may indicate that pharmacy work has been verified in any of a number of different ways, according to various embodiments. For example, in one embodiment, a pharmacist may graphically insert a notation into one or more of the images as an indication that the work displayed in the images has been supervised and/or verified. Alternatively, a pharmacist may electronically initial one or more of the captured images. In another embodiment, the verifying pharmacist may create a document referencing the captured images and a relevant pharmacy or medication order and indication that the corresponding pharmacy work was been verified according to the captured images. Such a document may be transmitted to an institutional pharmacy or may be uploaded to and stored on system website 130, according to various embodiments.

Additionally, an electronic record or a hard copy of the verified captured image(s) may be stored at the remote pharmacist site, and/or at system website 130. In yet another example, a pharmacist may utilize digital signature technology to digitally sign one or more of the captured images or another document indicating pharmacist verification of the pharmacy work performed according to the captured images. In another embodiment, an indication that the pharmacist verified the pharmacy work according to the captured images may be transmitted to preparation site 120, either directly or indirectly. For example, a document including such an indication may be emailed or faxed to preparation site 120.

The pharmacist at a remote pharmacist site may also transmit the electronically notated image(s), or a copy thereof, from remote pharmacist site 110 to preparation site 120 via an Internet connection, virtual private network, or any wired or wireless link, in one embodiment. This may be done to communicate to non-pharmacist personnel that the work passed supervision, is verified, and is authorized for removal from the pharmacy or to be placed into regular pharmacy stock, according to some embodiments. The image may be further notated at the preparation site 120 and an electronic or hard copy record of the supervised and verified image may be stored at preparation site 120.

Additionally, at remote pharmacist site 110, the supervised, verified, and pharmacist-initialed captured images, or other document(s) indicating that the pharmacy work was correctly verified, may be printed, such as on printer 330 and/or transmitted to preparation site 120 via facsimile or other method, such as email. The facsimile may be received in the pharmacy at preparation site 120. A nurse or other personnel may review the verified documents and verify that it has the pharmacist's initials, which may authorize her to remove the medication from the pharmacy, according to some embodiments. She may write a removal time on the papers and store them in an appropriate place so the next pharmacist on duty at the facility may review and/or file the papers for the pharmacy's records.

If, during the supervision and verification process, a pharmacist at remote pharmacist site 110 discovers, through inspection of the captured images, errors in the work performed by the non-pharmacist, the pharmacist may notify both the non-pharmacist who performed the work, as well as other supervisory personnel, about the errors so that corrective measures may be taken, according to some embodiments.

Figure 15:
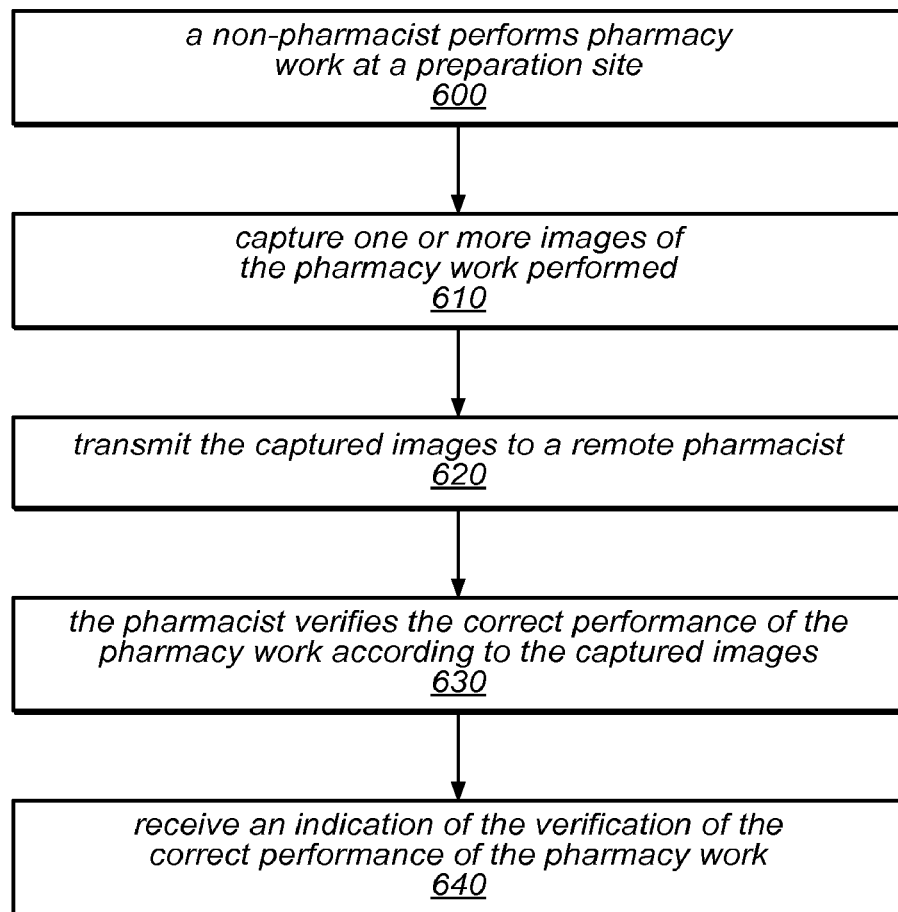
FIG. 15 is a flowchart illustrating a method for remotely supervising and verifying pharmacy functions, according to one embodiment.

FIG. 15 illustrates one embodiment of a method for remotely supervising and verifying pharmacy work performed by a non-pharmacist. As described above, a non-pharmacist may perform pharmacy work at an institutional pharmacy for a pharmacy work task requiring pharmacist supervision, verification or both, as illustrated by block 600. For instance, an institution, such as a hospital or correctional facility, may not have a pharmacist on duty all the time and a patient may require medication that can only be obtained through the institution's pharmacy. Thus, a non-pharmacist, such as a nurse or pharmacy technician, may perform the pharmacy functions required to fulfill the order. Pharmacy functions that may be remotely supervised and verified include, but are not limited to, medication preparation, packaging, prepackaging, compounding, and/or labeling of either single unit packages, multiple dose packages, in batches or in bulk. The non-pharmacist may capture one or more images of the pharmacy work, as illustrated by block 610. Images of pharmacy work may be captured at various times during the performance of the pharmacy work, in some embodiments. In other embodiments, images may be captured of the finished medication product and all materials and documentation required for the performing the pharmacy work, as described herein above.

The captured images may be transmitted to a remote pharmacist, as illustrated by block 620. Thus, as described above, the captured images may be sent to a remote pharmacist for remote supervision and review, as described above. For example, the images may be sent directly to the remote pharmacist via email, in one embodiment. In other embodiments, the captured images may be uploaded to a website from which the remote pharmacist may download them. Additionally, other documentation may also be sent to the pharmacist either by email, uploading to a website, via fax, or by any suitable means. After receiving the captured images, the remote pharmacist may verify the correct performance of the pharmacy work according to the captured images, as illustrated by block 630. For instance, the pharmacist may examine the captured images and other documents to ensure that the correct ingredients, materials, and measures were used when performing the various pharmacy functions. If the pharmacist is able to conduct process checks and verify that the pharmacy work was correctly performed, she may indicate such by initialing, labeling, or digitally signing one or more of the captured images, according to one embodiment. In other embodiments, the pharmacist may indicate the verification that the pharmacy work was correctly performed according to the captured images by creating a separate verification document or record. The pharmacist may send such verification to the institutional pharmacy.

The institutional pharmacy may receive an indication of the verification of the correct performance of the pharmacy work, as illustrated by block 640. For instance, the pharmacist may email an indication that the pharmacy work was verified, or alternatively, may upload such an indication to system website 130 from which the institutional pharmacy may download it, according to different embodiments. Alternatively, in another embodiment, the pharmacist may fax such an indication to the institutional pharmacy. After receiving an indication that the remote pharmacist verified the pharmacy work, the medication or other pharmacy product produced by the pharmacy work may be further processed or removed from the work area In various embodiments, the systems and procedures described above can be used in an instructional environment. In one embodiment, pharmacy technician students in a laboratory perform lab activities and capture images of their work. For example, the students may perform lab modules involving med prep, packaging, etc. The systems used to capture images may include, for example, one or more of the systems described in FIGS. 2-10. The student's work may be checked and graded at a later time by a pharmacist instructor(s).

Figure 16:
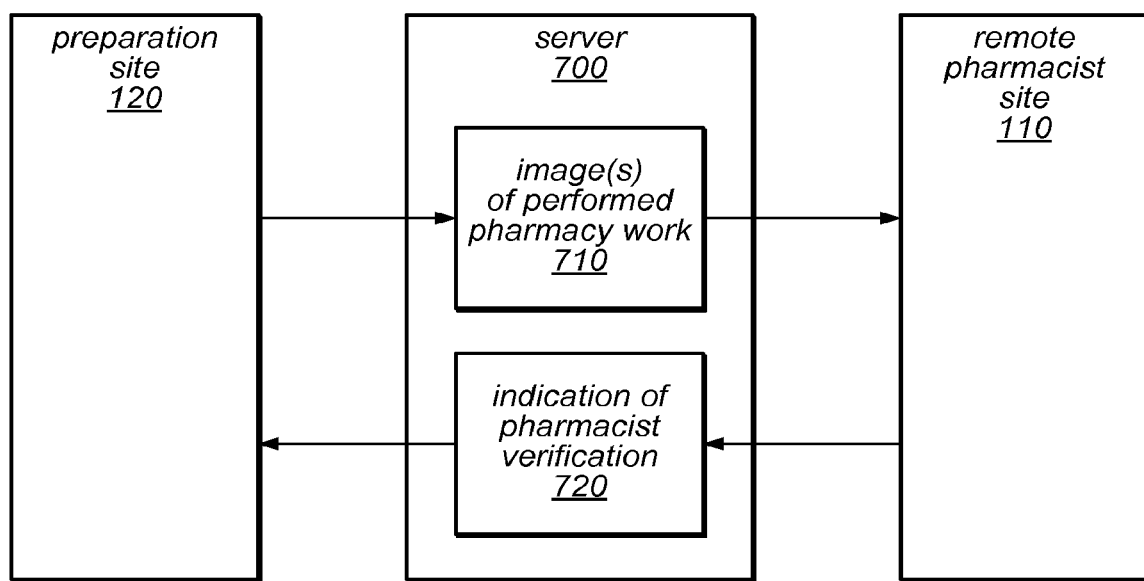
FIG. 16 is a block diagram illustrating a server facilitating remote supervision and verification of pharmacy functions, in one embodiment.

As noted above, in some embodiments, a remote pharmacist may remotely supervise and verify pharmacy functions according to images of the performed pharmacy work that transmitted directly between a preparation site and the remote pharmacist. In other embodiments, however, preparation sites and remote pharmacists may use a network addressable server, such as may be part of system website 130, to communicate and transfer images and/or other data or documents related to remotely verifying pharmacy functions. FIG. 16 is a block diagram illustrating the use of server 700 by preparation site 120 and remote pharmacist site 110 for communication and data (image) exchange as part of remote verification of pharmacy functions. Server 700 may be located at preparation site 120, remote pharmacist site 110, or at a location separate from either preparation site 120 or remote pharmacist site 110, according to various embodiments. Server 700 may be addressable via network 100, which in some embodiments, may be the Internet. In other embodiments, however, server 700 may be accessible via other methods, such as via a corporate LAN/WAN, direct modem communication, or other wired or wireless technology. In some embodiments, server 700 may be a web server, while, in other embodiments, server 700 may be a bulletin board system allowing posts and retrieval of images and/or other documents. Server 700 may provide security, such as requiring user names and passwords, or other user authentication, to prevent unauthorized accessing of pharmacy related images or information. In general, server 700 may utilize any of numerous data and communication security techniques, such as encryption, user authentication, HTTPS communication, etc.

When utilizing a server, such as server 700, for communication related to remote verification of pharmacy functions, the non-pharmacist performing the pharmacy work may upload or transmit one or more images of performed pharmacy work (or, alternatively, images of the work as it is being performed), to server 700. For example, in one embodiment, images may be transmitted via FTP or another network file transfer protocol. Server 700 may then store the received images for later access by a remote pharmacist. In some embodiments, the images may be associated with a job or task identifier that may be used by a pharmacist to reference the images for review.

Server 700 may also provide an interface for review of images by pharmacists, according to some embodiments. For instance, server 700 may notify the pharmacist that the images have been stored and are available for review. Server 700 may also allow the pharmacist to download or otherwise retrieve the images from server 700 for review locally on the pharmacist's computer. Alternatively, in another embodiment, server 700 may provide an interface for online reviewing of images. For example, server 700 may generate web pages allowing a pharmacist to view the stored images of performed pharmacy work with a standard web browser program without having to retrieve or save the images locally.

After reviewing the images to verify whether the pharmacy work was performed correctly, a pharmacist may upload to server 700 an indication of the verification, according to the images, of the pharmacy work performed. For example, in one embodiment, the pharmacist may upload a copy of one or more of the images to which the pharmacist's digital signature is attached as an indication of the verification of the pharmacy work. In another embodiment, however, the pharmacist may upload a separate document including an indication of his verification of the pharmacy work. In yet another embodiment, server 700 may provide an interface, such as via generated web pages, allowing a pharmacist to record on server 700 an indication of the verification of the pharmacy work according to the images.

Server 700 also may, in some embodiments, notify the non-pharmacist that the pharmacist has recorded or uploaded an indication of the verification of the pharmacy work. Thus, server 700 may direct the communication between the non-pharmacist at the preparation site and the remote pharmacist. Additionally, server 700 may provide an interface for the institutional pharmacy to access, view, and/or download the pharmacist's indication that the pharmacy work was verified. Server 700 may provide an interface allowing a non-pharmacist or institutional pharmacy to download whatever data or documents were stored on server 700 by the pharmacist, according to one embodiment. Alternatively, server 700 may allow personnel at the preparation site, such as an institutionally pharmacy, to view data and/or documents from the remote pharmacist site online without having to download and store them locally at the preparation site. For example, in one embodiment, server 700 may generate web pages allowing review of data and/or documents stored on server 700 by a remote pharmacist.

Using a server, or other shared storage area, for communication between an preparation site, and a remote pharmacist may also facilitate review and/or supervision of the remote verification process by administrators or others. For instance, server 700 may provide an interface allowing a director of an institutional pharmacy to access, examine and/or review the images from the institutional pharmacy as well as any data or documents from remote pharmacists. Additionally, server 700 may be configured to work in conjunction with other software on workstations at preparation sites and/or remote pharmacist sites. For example, custom software, such as remote verification software 140, configured specifically for communication and data exchange as part of remote verification of pharmacy functions may provide a user interface for uploading, downloading, and/or reviewing images stored on server 700, according to one embodiment.

Figure 17:
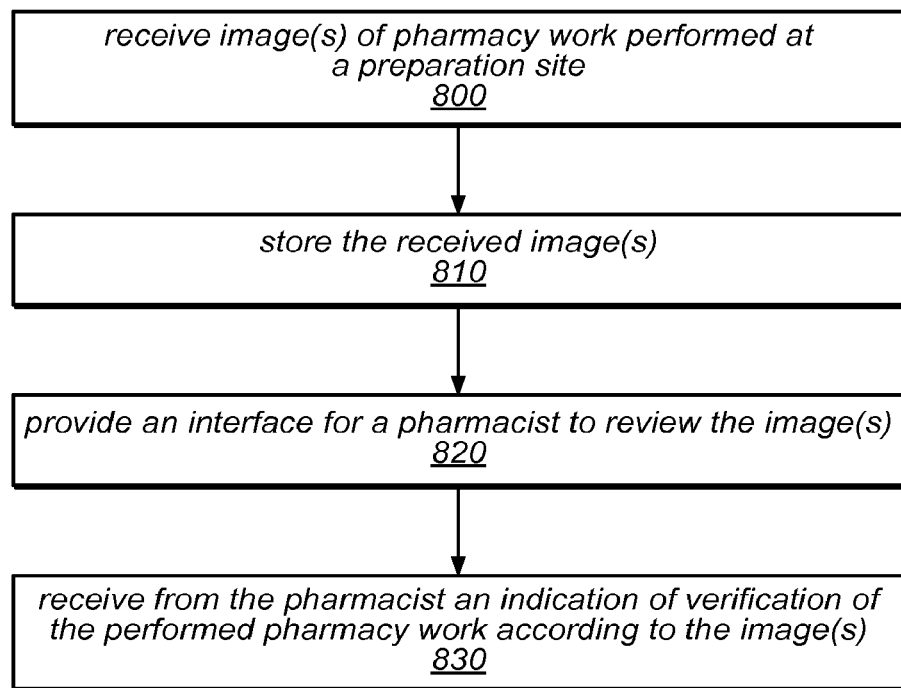
FIG. 17 is flowchart illustrating one embodiment of a method for utilizing a network accessible server for remote supervision and verification of pharmacy functions.

FIG. 17 illustrates a flowchart for one embodiment of a method for a server, such as server 700 described above, to facilitate remote supervision of pharmacy functions, as described herein. For instance, server 700 may receive one or more images of pharmacy work performed by a non-pharmacist at an institutional pharmacy, such as institutional pharmacy 120, as illustrated by block 800. As noted above, images of performed pharmacy work maybe uploaded, posted, or otherwise transmitted to server 700. Server 700 may store the received images for later access, retrieval, and/or review, as illustrated by block 810. Server 700 may store received images in any of variety of manners and formats, according to various embodiments. Images may be stored as individual files on a file server, as records in an image database, or multiple images may be compacted and stored together in a single file, such as in a .ZIP file, in some embodiments.

Server 700 may also provide an interface for a remote pharmacist, such as one at remote pharmacist site 110, to review the images, as illustrated by block 820. For example, in one embodiment, server 700 may provide a web interface, consisting of one or more generated web pages, allowing a remote pharmacist to review images using a standard web browser program. In another embodiment, server 700 may implement a messaging interface allowing custom software for remote verification of pharmacy functions, such as remote verification software 140, to send messages requesting the storage or retrieval of images, documents or other data. In general, server 700 may allow a remote pharmacist to access the images stored on server 700 by an institutional pharmacy.

After reviewing the pharmacy work according to the images, a pharmacist may record or store on server 700 an indication of his verification of the pharmacy work. Thus, server 700 may receive from the pharmacist an indication of verification of the performed pharmacy work according to the images, as illustrated by block 830. In some embodiments, server 700 may provide an interface allowing the pharmacist to record such an indication. In another embodiment, the pharmacist may upload a document or image including such an indication. For example, the pharmacist may attach a digital signature or other digital certificate to one or more of the images and upload the image(s) to server 700 and the institutional pharmacy may be able to download or otherwise access the pharmacist's indication. Alternatively, the pharmacist may generate and store a separate document including an indication of the verification of the performed pharmacy work. In some embodiments, such a document may include details of the verification or may include issues or problems discovered in the performance of the pharmacy functions.

Server 700 may, in some embodiments, notify an institutional pharmacy, such as via email or instant messenger, that the pharmacist has finished reviewing the stored images and has recorded an indication of his verification of the pharmacy function according to the images. Additionally, server 700 may implement or provide an interface allowing an institutional pharmacy to access and/or review results of the pharmacist's verification. For example, in one embodiment, server 700 may allow custom software, such as remote verification software 140 to access and/or download the data or documents stored by a remote pharmacist. Alternatively, server 700 may implement a web page based interface allowing an institutional pharmacy to review data and/or documents stored on server 700 by a remote pharmacist.

Figure 18:
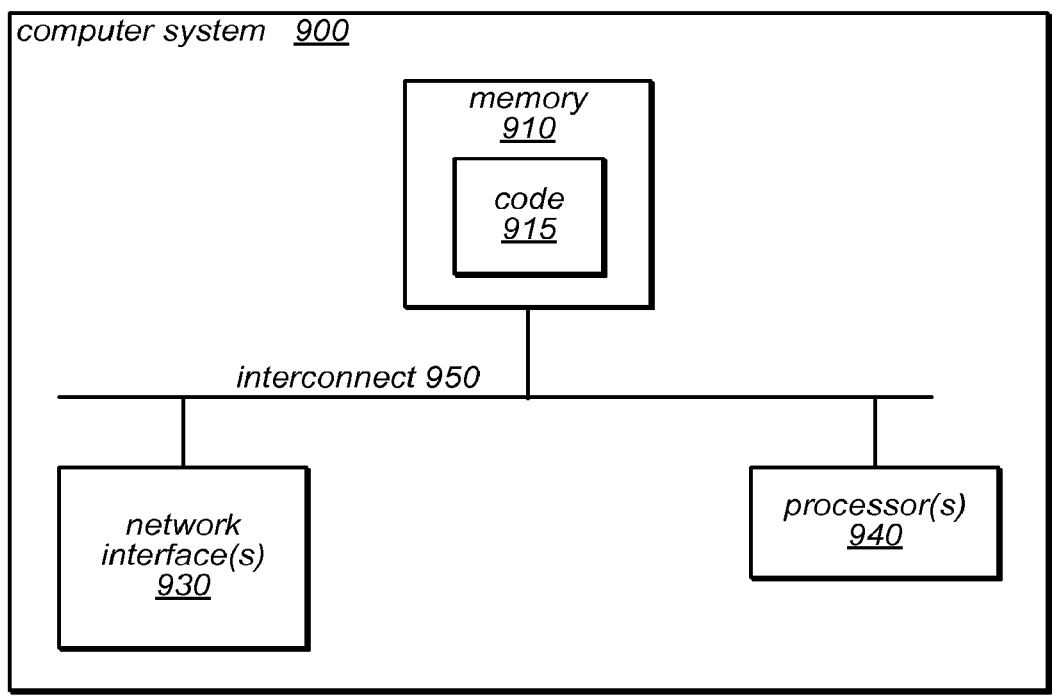
FIG. 18 is a block diagram illustrating an exemplary computer system suitable for implementing remote supervision and verification of pharmacy functions, according to one embodiment.

FIG. 18 is a block diagram illustrating an embodiment of a computer system usable to implement remote pharmacy supervision and verification. In some embodiments, a workstation at either preparation site 120, remote pharmacist site 110, system website 130, and/or server 700, may include a general-purpose computer system that includes or is configured to access one or more computer-accessible media, such as computer system 900 illustrated in FIG. 18. In the illustrated embodiment, computer system 900 includes one or more processors 940 coupled to a system memory 910 via an interconnect 950. Computer system 900 may further includes a network interface 930 also coupled to interconnect 950.

In various embodiments, computer system 900 may be a uniprocessor system including one processor 940, or a multiprocessor system including several processors 940 (e.g., two, four, eight, or another suitable number). Processors 940 may be any suitable processors capable of executing instructions. For example, in various embodiments, processors 940 may be general-purpose or embedded processors implementing any of a variety of instruction set architectures (ISAs), such as the x86, PowerPC, SPARC, or MIPS ISAs, or any other suitable ISA. In multiprocessor systems, each of processors 940 may commonly, but not necessarily, implement the same ISA.

System memory 910 may be configured to store instructions and data accessible by processor 940. In various embodiments, system memory 910 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those methods and techniques described above for remotely supervising and verifying pharmacy functions, may be stored within system memory 910 as code 915.

In one embodiment, interconnect 950 may be configured to coordinate I/O traffic between processor 940, system memory 910, and any peripheral devices in the device, including network interface 930 or other peripheral interfaces. In some embodiments, interconnect 950 may perform any necessary protocol, timing or other data transformations to convert data signals from one component (e.g., system memory 910) into a format suitable for use by another component (e.g., processor 940). In some embodiments, interconnect 950 may include support for devices attached through various types of peripheral buses, such as a variant of the Peripheral Component Interconnect (PCI) bus standard or the Universal Serial Bus (USB) standard, for example. In some embodiments, the function of interconnect 950 may be split into two or more separate components, such as a north bridge and a south bridge, for example. Also, in some embodiments some or all of the functionality of interconnect 950, such as an interface to system memory 910, may be incorporated directly into processor 940.

Network interface 930 may be configured to allow data to be exchanged between computer system 900 and other devices attached to a network, such as other computer systems, for example. Network interface 930 may commonly support one or more wireless networking protocols (e.g., Wi-Fi/IEEE 802.11, or another wireless networking standard). However, in various embodiments, network interface 930 may support communication via any suitable wired or wireless general data networks, such as other types of Ethernet network, for example. Additionally, network interface 930 may support communication via telecommunications/telephony networks such as analog voice networks or digital fiber communications networks, via storage area networks such as Fibre Channel SANs, or via any other suitable type of network and/or protocol.

In some embodiments, system memory 910 may be one embodiment of a computer-accessible medium configured to store program instructions and data as described above. However, in other embodiments, program instructions and/or data may be received, sent or stored upon different types of computer-accessible media. Generally speaking, a computer-accessible medium may include storage media or memory media such as magnetic or optical media, e.g., disk or DVD/CD coupled to computer system 900 via interconnect 950. A computer-accessible medium may also include any volatile or non-volatile media such as RAM (e.g. SDRAM, DDR SDRAM, RDRAM, SRAM, etc.), ROM, etc, that may be included in some embodiments of computer system 900 as system memory 910 or another type of memory.

The various methods as illustrated in the figures and described herein represent exemplary embodiments of systems and methods. The systems and methods may be implemented manually, in software, in hardware, or a combination thereof. The order of any method may be changed, and various elements may be added, reordered, combined, omitted, modified, etc. Additionally, various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system for acquiring images of a process of preparing a sterile compounded medication performed by a non-pharmacist person, comprising:
    a pharmaceutical preparation surface configured to be placed within a hood;

a camera assembly comprising:
  a camera configured to capture one or more images of one or more components of the sterile compounded medication placed on the pharmaceutical preparation surface; and
  a housing configured to hold the camera above the pharmaceutical preparation surface, the housing comprising at least one seal to inhibit fluids outside the housing from reaching the camera;
a display;
a trigger operatively connected to the camera;
a barcode scanner;
a processor in communication with the camera, the display, the trigger, and the barcode scanner; and
memory having stored thereon programming instructions that, when executed by the processor, cause the processor to:
  receive ingredient data associated with an ingredient of a sterile compounded medication;
  compare the ingredient data with patient medication data and determine if the ingredient data matches the patient medication data;
  provide, based on the determination, a first indication that compounding can continue when the ingredient data matches the patient medication data and a second indication that compounding cannot continue when the ingredient data does not match the patient medication data;
  capture, with the camera and based on receipt of a trigger signal from the trigger, one or more images of the one or more components of the sterile compounding process;
  receive the one or more captured images from the camera;
  associate the one or more captured images with the patient medication data; and
  transmit the one or more captured images and at least a portion of the associated patient medication data to a server; and
  receive, from the server, approval data indicating that a step of the sterile compounding process has been verified.

2. The system according to claim 1, further comprising a printer in communication with the processor.

3. The system according to claim 2, wherein the programming instructions, when executed by the processor, cause the processor to:
  control the printer to print a document comprising at least a portion of the approval data.

4. The system according to claim 1, wherein the housing is moveable relative to the pharmaceutical preparation surface.

5. The system according to claim 1, wherein the trigger is a manual trigger.

6. The system according to claim 1, wherein the trigger is a foot pedal.

7. The system according to claim 1, wherein the programming instructions, when executed by the processor, further cause the processor to:
  display one or more instructions for preparing the sterile compounded medication.

8. The system according to claim 1, wherein the ingredient data is received from the barcode scanner.

9. The system according to claim 8, wherein the programming instructions, when executed by the processor, further cause the processor to:
  extract the ingredient data from a barcode present on a container holding the ingredient.

10. The system according to claim 9, wherein the programming instructions that cause the processor to compare the ingredient data with the patient medication data cause the processor to identify the ingredient by querying a drug code database based on the extracted ingredient data.

11. A system for acquiring images of a process of preparing a sterile compounded medication performed by a non-pharmacist person, comprising:
a pharmaceutical preparation surface configured to be placed within a hood;
a camera assembly comprising:
  a camera configured to capture one or more images of one or more steps of the process, including one or more components of the sterile compounded medication placed on the pharmaceutical preparation surface; and
  a housing configured to hold the camera above the pharmaceutical preparation surface, the housing comprising at least one seal to inhibit fluids outside the housing from reaching the camera;
a display;
a manual trigger operatively connected to the camera;
a printer;
a barcode scanner;
a processor in communication with the camera, the display, the manual trigger, the printer, and the barcode scanner; and
memory having stored thereon programming instructions that, when executed by the processor, cause the processor to:
  receive, from the barcode scanner, barcode data associated with an ingredient of a sterile compounded medication;
  extract the ingredient data from the barcode data;
  compare the ingredient data with patient medication data and determine if the ingredient data matches the patient medication data;
  provide, based on the determination, a first indication that compounding can continue when the ingredient data matches the patient medication data and a second indication that compounding cannot continue when the ingredient data does not match the patient medication data;
  capture, with the camera and based on receipt of a trigger signal from the trigger, one or more images of the one or more components of the sterile compounding process;
  receive the one or more captured images from the camera;
  associate the one or more captured images with the patient medication data; and
  transmit the one or more captured images and at least a portion of the associated patient medication to a server;
  receive, from the server, approval data indicating that the step of the sterile compounding process has been verified; and
  print a document including the approval data.

12. The system according to claim 11, wherein the housing is moveable relative to the pharmaceutical preparation surface.

13. The system according to claim 11, wherein the manual trigger is a foot pedal.

14. The system according to claim 11, wherein the programming instructions, when executed by the processor, further cause the processor to:
   display one or more instructions for preparing the sterile compounded medication.

15. The system according to claim 11, wherein the programming instructions that cause the processor to compare the ingredient data with the patient medication data cause the processor to identify the ingredient by querying a drug code database based on the extracted ingredient data.

* * * * *